US012731806B2

(12) United States Patent
Ekkert et al.

(10) Patent No.: US 12,731,806 B2
(45) Date of Patent: Sep. 8, 2026

(54) ELECTROLYTE REGENERATION FOR ORGANIC REDOX FLOW BATTERIES BASED ON WATER-SOLUBLE PHENAZINE-BASED COMPOUNDS

(71) Applicant: CMBLU Energy AG, Alzenau (DE)

(72) Inventors: Olga Ekkert, Hanau (DE); Evgeny Larionov, Hanau (DE); Jan Hartwig, Alezenau (DE); Eduard Baal, Offenbach (DE)

(73) Assignee: CMBLU Energy AG, Alzenau (DE)

( * ) Notice: Subject to any disclaimer, the term of this patent is extended or adjusted under 35 U.S.C. 154(b) by 570 days.

(21) Appl. No.: 18/031,751

(22) PCT Filed: Nov. 30, 2020

(86) PCT No.: PCT/EP2020/083927
§ 371 (c)(1),
(2) Date: Aug. 31, 2023

(87) PCT Pub. No.: WO2022/111833
PCT Pub. Date: Jun. 2, 2022

(65) Prior Publication Data

US 2023/0411662 A1 Dec. 21, 2023

(51) Int. Cl.
*H01M 8/18* (2006.01)
*C01C 3/12* (2006.01)
(Continued)

(52) U.S. Cl.
CPC ............... *H01M 8/188* (2013.01); *C01C 3/12* (2013.01); *C07D 241/46* (2013.01); *H01M 8/04276* (2013.01)

(58) Field of Classification Search
CPC ..... H01M 8/188; H01M 8/04276; C01C 3/12; C07D 241/46
See application file for complete search history.

(56) References Cited

U.S. PATENT DOCUMENTS 1,916,627 A 7/1933 Mersch
1,963,383 A 6/1934 Rogers
(Continued)

FOREIGN PATENT DOCUMENTS

CN 101475758 A 7/2009
CN 102040483 A 5/2011
(Continued)

OTHER PUBLICATIONS

Machine Translation of CN-103762377-B (Nov. 23, 2025) (Year: 2025).*
(Continued)

*Primary Examiner* — Matthew J Merkling
(74) *Attorney, Agent, or Firm* — Harness Dickey & Pierce P.L.C.

(57) ABSTRACT

The present invention provides a process for the regeneration of an electrolyte solution of a redox-flow battery containing at least one (preferably substituted) phenazine compound, said process comprising at least one of the following steps (a), (b) and (c): (a) treatment of the electrolyte solution to be regenerated in order to convert organic degradation compounds contained therein to a (substituted) phenazine compound; (b) removal of precipitated material from the electrolyte solution and subsequent modification of the precipitated organic degradation compounds to obtain a (substituted) phenazine compound; and (c) separation of redox active compounds other than (substituted) phenazine compounds in particular inorganic electrolytes, from an electrolyte solution containing (substituted) phenazine compounds, and/or separation of (substituted) phenazine compounds from a solution containing redox active compounds other than (substituted) phenazine compounds.

5 Claims, 1 Drawing Sheet

DHPS
MHPS
DHP
MHP

(51) Int. Cl.
*C07D 241/46* (2006.01)
*H01M 8/04276* (2016.01)

(56) References Cited

U.S. PATENT DOCUMENTS 3,389,124 A 6/1968 Sparks
3,646,071 A 2/1972 Frey et al.
4,124,606 A 11/1978 Anello et al.
4,420,644 A 12/1983 Huibers et al.
4,579,943 A 4/1986 Kamide et al.
4,608,435 A 8/1986 Howell
4,956,244 A 9/1990 Shimizu et al.
4,973,720 A 11/1990 Saito et al.
5,002,634 A 3/1991 Dimmel et al.
5,049,477 A 9/1991 Nakamura et al.
5,712,416 A 1/1998 Gessner
5,723,675 A 3/1998 Joo et al.
5,932,752 A 8/1999 Keshavaraja et al.
5,944,953 A 8/1999 Lavoie et al.
9,548,509 B2 1/2017 Anderson et al.
10,777,836 B1 * 9/2020 Wei .................. H01M 8/04201
11,008,284 B2 5/2021 Krawczyk et al.
11,225,756 B2 1/2022 Krawczyk et al.
11,450,854 B2 9/2022 Hartwig et al.
11,731,945 B2 8/2023 Geigle et al.
2001/0028977 A1 10/2001 Kazacos et al.
2004/0244925 A1 12/2004 Tarasenko
2006/0183016 A1 8/2006 Kazacos et al.
2006/0263697 A1 * 11/2006 Dahn ................ H01M 10/0567 29/623.1
2007/0073076 A1 3/2007 Lewis et al.
2010/0086675 A1 4/2010 Berta et al.
2011/0144337 A1 6/2011 Santhosh et al.
2011/0268652 A1 11/2011 Machhammer et al.
2012/0045680 A1 2/2012 Dong et al.
2013/0079566 A1 3/2013 Lin
2013/0084482 A1 * 4/2013 Chang ................. H01M 8/0693 429/107
2013/0116424 A1 5/2013 Peterson et al.
2013/0232852 A1 9/2013 Peterson et al.
2013/0232853 A1 9/2013 Peterson et al.
2014/0028261 A1 1/2014 Esswein et al.
2014/0370403 A1 12/2014 Narayan et al.
2014/0370405 A1 * 12/2014 Zhang ..................... H01M 8/20 429/418
2015/0243991 A1 8/2015 Huskinson et al.
2016/0009621 A1 1/2016 Blair
2016/0013497 A1 1/2016 Jones et al.
2016/0032525 A1 2/2016 Kurple et al.
2016/0130752 A1 5/2016 Stigsson et al.
2016/0197371 A1 7/2016 Takechi
2016/0301084 A1 10/2016 Gendel et al.
2017/0162916 A1 6/2017 Guarr et al.
2018/0079721 A1 3/2018 Armand et al.
2018/0097249 A1 4/2018 Narayan et al.
2018/0099917 A1 4/2018 Anthony et al.
2018/0366757 A1 12/2018 Wei et al.
2018/0375142 A1 12/2018 Zhang et al.
2019/0152902 A1 5/2019 Krawczyk et al.
2019/0245233 A1 8/2019 Pintauro et al.
2019/0390405 A1 12/2019 Geigle et al.
2019/0393506 A1 12/2019 Hartwig et al.
2020/0014040 A1 1/2020 Kerker et al.
2020/0283380 A1 9/2020 Krawczyk et al.
2020/0373597 A1 11/2020 Perry et al.
2021/0020943 A1 1/2021 Hartwig et al.
2021/0024453 A1 1/2021 Hartwig et al.
2021/0083310 A1 * 3/2021 Perry ................. H01M 8/0488
2021/0276945 A1 9/2021 Krawczyk et al.
2022/0048869 A1 * 2/2022 Lee ...................... C07D 241/46
2023/0095542 A1 3/2023 Geigle et al.
2023/0097730 A1 3/2023 Geigle et al.
2023/0130406 A1 4/2023 Hartwig et al.
2023/0304221 A1 9/2023 Krawczyk et al.
2024/0014409 A1 1/2024 Geigle et al.
2024/0014427 A1 1/2024 Ekkert et al.
2024/0222674 A1 7/2024 Geigle et al.
2024/0270672 A1 8/2024 Geigle et al.
2024/0318382 A1 9/2024 Krawczyk et al.
2024/0356030 A1 10/2024 Hartwig et al.
2025/0263384 A9 8/2025 Geigle et al.

FOREIGN PATENT DOCUMENTS

CN 103000924 A 3/2013
CN 104005046 A 8/2014
CN 103762377 B * 3/2016 .......... H01M 8/0482
CN 107425212 A * 12/2017 ............ H01M 8/188
EP 3492628 A1 6/2019
FR 3030561 A1 6/2016
GB 1086522 A 10/1967
GB 1502275 A 3/1978
JP S51100064 A 9/1976
JP S51138666 A 11/1976
JP S52144662 A 12/1977
JP H01115068 A 5/1989
JP H06260204 A 9/1994
JP H9227499 A 9/1997
JP 3813864 B2 8/2006
JP 2011057636 A 3/2011
JP 2013254685 A 12/2013
JP 2019503619 A 2/2019
JP 2020021732 A 2/2020
RO 76126 A2 5/1981
SU 1129204 A1 12/1984
WO 1993006626 A1 4/1993
WO 1998/013538 A1 4/1998
WO 2011111717 A1 9/2011
WO 2011131959 A1 10/2011
WO 2011142838 A2 11/2011
WO WO2013131838 A1 9/2013
WO 2014081235 A1 5/2014
WO 2014204985 A1 12/2014
WO 2015048550 A1 4/2015
WO 2015148357 A1 10/2015
WO 2016144909 A1 9/2016
WO 2017174098 A1 10/2017
WO 2018152436 A1 8/2018
WO 2018231926 A1 12/2018
WO 2019240933 A1 12/2019
WO 2020035138 A1 2/2020
WO 2020035549 A2 2/2020
WO 2020201405 A1 10/2020

OTHER PUBLICATIONS

Machine Translation of CN-107425212-A (Nov. 23, 2025) (Year: 2025).*

Charalambous, et al. (1977). Deoxygenation of 2-Nitrosophenols and of their Metal Complexes with Triphenyphosphine. Sytnthesis of Phenzaines, Dihydrophenazines, Triphenyl(o-hydroxyphenylimino)phosphoranes and their Metal Complexes, Journal of The Chemical Society, 400-401.

Gao Xiaochun et al. (2013). Synthesis and anti cancer activity of some novel 2-phenazinamine derivatives, European Journal of Medicinal Chemistry, 69: 1-9.

Laha J.K., et al. (2014). Transition-Metal-Free Tandem Oxidative Removal of Benzylic Methylene Group by C—C and C—N Bond Cleavage Follwed by Intramolecular New Aryl C—N Bond Formation under Radical Conditions, Org. Lett. 17: 4392-4395.

Salomi B.S: et al. (2007). Electrochemical studies of horseradish peroxidase covalently coupled with redox dyes, Biosensors • nd Bioelectronics, 22(8): 1825-1829.

Tabor, Daniel P (2018). Approaching saturation limits, Nature Energy, 3:455-456.

Maiers, W.A. et al. (1959). The reaction of phenazine with free benzyl radicals, J_ Chem. Soc., 2085-2087.

V'oshioka I., et al. (1964). Studies on Phenazines. XXV. On the Bromination of 1-and 2-Methylphenazine by N-Bromosuccinimide. (1), Chem Pharm Bull (Tokyo).

(56) References Cited

OTHER PUBLICATIONS

Lange, A et al. (1981). The Electronic Spectra of Aminophenazines, Ber.Bunsenges.Phys.Chem. 85: 78-85.
Nagai, K et al. (1991). DNA Cleavage by Oxygen Radicals Produced in the Absence of Metal lons or Light, J. Am. Chem. Soc., 113: 5099-5100.
Martin, D.A. et al. (2017). White light induced colvalent modification of graphene using a phenazine dye, Chem. Commun. 53:10715-10718.
Zamaratski, E. et al. (1998). Synthesis of Phenazine-tethered Arabino and Zylofuranosyl Oligonucleotide Conjugates: The Thermal Stability and Flourescence Properties of Their Duplexes (DNA-DNA & DNA-RNA) & Triplets, Tetrahedron 54: 8183-8206.
Dilung, I.I. et al. (1984). Scientific selection of photopolymerization initiators for information recording, Visnik Akademii Nauk Ukrains'koi RSR, 12:15-23.
Non-Final Office Action from U.S. Appl. No. 17/799,879 dated Jan. 31, 2025.
Final Office Action from U.S. Appl. No. 17/799,879 dated May 19, 2025.
Arai, G., and Onozuka, M., "The Reaction of 1, 4-Naphthoquinone-2-sulfonate with Sodium Sulfite," The Chemical Society of Japan, 12: 1899-1903, (1981).
Azarov, V.I., "Khimiya drevesiny i sinteticheskikh polimerov," Sankt-Petersburg, pp. 366-373 (1999).
Brauns, F.E., "Khimiya lignina," Moscow, pp. 558-570 (1964).
Denisov, E.T., and Metelitsa, D.I., "Oxidation of Benzene," Russ. Chem. Rev., 37 (656), 1968.
Dominguez-Ramos, A., et al., "Electrochemical Oxidation of Lignosulfonate: Total Organic Carbon Oxidation Kinetics," Ind. Eng. Chem. Res., 47(24): 9848-9853 (2008).
Dorn, Bv H. W., et al., "Certain Derivatives of the Ethers of Hydroxyhydroquinone," Journal of the American Chemical Society, 61: 144-147 (1939).
Duval, A., et al., "Fractionation of lignosulfonates: comparison of ultrafiltration and ethanol solubility to obtain a set of fractions with distinct properties," Holzforschung, 69(2): 127-134 (2015).
Fitzky, H.G., et al., "Paramagnetic electron resonance measurements fo short-lived, substituted p-benzosemiquinones," Photographische Korrespondenz, 103(4): 60-64 (1967).
Gierer, J., "Chemistry of delignification, Part 1: General concept and reactions during pulping," Wood Science and Technology, 19: 289-312 (1985).
Gierer, J., "Chemistry of delignification: Part 2: Reactions of lignins during bleaching," Wood Science and Technology, 20: 1-33 (1986).
Hu L., et al., "Methods to Improve Lignin's Reactivity as a Phenol Substitute and as Replacement for Other Phenolic Compounds: A Brief Review," Bio Resources, 6(3): 3515-3525 (2011).
Huber, G. W., et al., "Synthesis of Transportation Fuels from Biomass: Chemistry, Catalysts, and Engineering," Chemical Reviews, American Chemical Society, 106: 4044-4098 (2006).
International Search Report from PCT Application No. PCT/EP2018/053595 dated Jun. 12, 2018.
International Search Report from PCT Application No. PCT/EP2018/053596 dated May 3, 2018.
International Search Report from PCT Application No. PCT/EP2018/053597 dated May 8, 2018.
International Search Report from PCT Application No. PCT/EP2019/053602 dated Apr. 3, 2019.
International Search Report issued in PCT/EP2017/000461 dated Dec. 6, 2017.
International Search Report issued in PCT/EP2017/000462 issued Sep. 6, 2017.
Mark, H. B., and Atkin, C. L., "Electrode Reactions of Aromatica Compounds in Strong Acid Solutions," Analytical Chemistry, 36(3): 514-520 (1964).
Miyazawa, T., et al., "Highly regioselective propanoylation of dihydroxybenzenes mediated by Candida antarctica lipase B in organic solvents," Tetrahedron Letters, 49: 175-178 (2008).
Moodley, B. et al., "The electro-oxidation of lignin in Sappi Saiccor dissolving pulp mill effluent," 37(1): 33-40 (2011).
Office Action dated Mar. 20, 2020 issued in U.S. Appl. No. 16/091,436.
Office Action from corresponding Eurasian Patent Application No. 201892234 dated Sep. 10, 2019.
Office Action from corresponding Japanese Application No. 2019-503619 dated Feb. 8, 2022.
Office Action from corresponding U.S. Appl. No. 16/480,956 dated Aug. 17, 2021.
Office Action from corresponding U.S. Appl. No. 16/480,958 dated Aug. 23, 2021.
Restriction Requirement from U.S. Appl. No. 16/091,437 dated Jun. 15, 2020.
Smook, Gary A., "Handbook for Pulp and Paper Technologists," Angus Wilde Publications, 2nd edition, chapters 7 and 8 (1992).
Vandenberghe A., and Willems J.F., "Sulphonation of Alkylhydroquinones," Bull. Soc. Chim. Belges, 74(9-10): 397-406 (1965).
Weatherbee, C., et al., "A New Approach to Tertiary b-Chloroalkylamines. Synthesis of b-Chloroalkylaminomethylhydroquinones1", Journal of Organic Chemistry, 21(10): 1138-1141 (1956).
Wedege, K., et al., "Organic Redox Species in Aqueous Flow Batteries: Redox Potentials, Chemical Stabilitiy and Solubility," Scientific Reports, 6(1): 1-13 (2016).
Weetall, H. H., et al., "Biotechnology and Bioengineering—A Direct Fuel Cell for the Production of Electricity from Lignin," vol. 27, No. 7, p. 1-11 (1985).
Written Opinion from PCT Application No. PCT/EP2018/053595 dated Jun. 12, 2018.
Written Opinion from PCT Application No. PCT/EP2018/053596 dated May 3, 2018.
Written Opinion from PCT Application No. PCT/EP2018/053597 dated May 8, 2018.
Written Opinion from PCT Application No. PCT/EP2019/053602 dated Apr. 3, 2019.
Examination Report from corresponding Australian Application No. 2017246493 dated May 3, 2023.
Notice of Allowance issued in corresponding U.S. Appl. No. 17/177,567 dated Sep. 21, 2022.
Huskinson et al., "A metal-free organic-inorganic aqueous flow battery," Nature, 505(7482):195-198 (2014).
Non-Final Office Action from U.S. Appl. No. 17/842,079 dated Nov. 24, 2023.
Non-Final Office Action from U.S. Appl. No. 18/197,415 dated Feb. 14, 2024.
Office Action from corresponding CA Appln. No. 3,017,989 dated Jun. 7, 2024.
Non-Final Office Action from U.S. Appl. No. 18/611,202 dated Sep. 29, 2024.
Bidman, T.A. (2004). Oxidation of 2-alkyl-5, 10-dihydrophenazines. Russ J Gen Chem 74: 1433-1434.
Wei, et al., (2016). A turn-on fluorescent chemosensor selectively detects cyanide in pure water and food sample, Tetrahedron letters, 57:2767-2771.
European Search Report received in corresponding European Patent Application No. 19 758 645.6 dated Aug. 28, 2023.
Hollas, et al., (2018). A biometrick high-capacity phenazine-based anolyte for acqueous organic redox fllow batteries, Nature Energy, 3: (6): 508-514.
Ninsberg et al. (2016). Tempo/Phenazine Combi-Molecule: A redox-active material for symmetric acqueous redox-flow batteries, ACS Energy Letters, 1(5): 976-980.
Intemational Search Report and Written Opinion received for International Application No. PCT/EP2021/054296 mailed on Mar. 16, 2021.
Non-Final Office Action from U.S. Appl. No. 17/799,877 dated Jul. 16, 2025.
International Search Report from corresponding PCT Application No. PCT/EP2021/087647 dated Apr. 11, 2022.
Written Opinion from corresponding PCT Application No. PCT/EP2021/087647 dated Apr. 11, 2022.

(56) References Cited

OTHER PUBLICATIONS

Sanchez-Diez, E., et al., "Redox flow batteries: Status and perspective towards sustainable stationary energy storage," Journal of Power Sources, 481: 1-23 (2020).
Zhou, M., et al., "Single-Molecule Redox-Targeting Reactions for a pH-Neutral Aqueous Organic Redox Flow Battery," Angew. Chem. Int. Ed., 59: 14286-14291 (2020).
Goulet, M., et al., Extending the Lifetime of Organic Flow Batteries via Redox State Management, Journal of the Americal Chemical Society, 141:8014-8019 (2019).
International Search Report received for International Application No. PCT/EP2020/083927 mailed on Aug. 2, 2021.
Written Opinion received for International Application No. PCT/EP2020/083927 mailed on Aug. 2, 2021.
Written Opinion issued in PCT/EP2017/000461 issued Dec. 6, 2017.
Written Opinion issued in PCT/EP2017/00462 issued on Sep. 6, 2017.
www.chem.uiuc.edu, "Oxidation of Phenols," (1999).
Xu, Ch. et al., "Lignin depolymerisation strategies: towards valuable chemicals and fuels," Chem Soc Rev. 43: 7485-7500 (2014).
Yang, B., et al., "An Inexpensive Aqueous Flow Battery for Large-Scale Electrical Energy Storage Based on Water-Soluble Organci Redox Couples," Journal of the Electrochemical Society, 161(9): A1371-A1380 (2014).
Zakzeski, J. et al., "The Catalytic Valorization of Lignin for the Production of Renewable Chemicals," Chem. Rev., 110: 3552-3599 (2010).
Zhang, S., et al., "An Organic Electroactive Material for Flow Batteries," Electrochimica Acta, 190: 737-743 (2016).
Zhou, Y. et al., "Methods To Improve Lignin's Reactivity as a Phenol Substitute and as Replacement for Other Phenolic Compounds: A Brief Review," BioResources, 6(3): 1-11 (2011).
Office Action from corresponding U.S. Appl. No. 16/480,958 dated Apr. 26, 2022.
Office Action from corresponding U.S. Appl. No. 16/484,301 dated Apr. 22, 2022.
Kaiho, A. et al., "Construction of the di(trimethylolpropane) cross linkage and the phenylnaphthalene structure coupled with selective ?-O-4 bond cleavage for synthesizing lignin-based epoxy resins with a controlled glass transition temperature," Green Chem., 18: 6526-6535 (2016).
Klein, I. et al., "Lignin depolymerization over Ni/C catalyst in methanol, a continuation: effect of substrate and catalyst loading," Catal. Sci. Technol., 5: 3242-3245 (2015).
Office Action issued in corresponding U.S. Appl. No. 16/480,958 dated Feb. 4, 2022.
Office Action issued in corresponding U.S. Appl. No. 16/480,958 dated Sep. 14, 2022.
Restriction Requirement issued in corresponding U.S. Appl. No. 16/484,301 dated Sep. 29, 2021.
Office Action issued in corresponding U.S. Appl. No. 16/484,301 dated Oct. 27, 2022.
Restriction Requirement issued in U.S. Appl. No. 16/968,732 dated Mar. 17, 2022.
Office Action issued in U.S. Appl. No. 16/968,732 dated Jun. 24, 2022.
Office Action issued in U.S. Appl. No. 16/968,732 dated Nov. 30, 2022.
Restriction Requirement issued in corresponding U.S. Appl. No. 16/480,956 dated Apr. 28, 2021.
Restriction Requirement issued in corresponding U.S. Appl. No. 16/091,436 dated Aug. 1, 2019.
Interview Summary issued in corresponding U.S. Appl. No. 16/091,436 dated Jun. 4, 2020.
Office Action issued in corresponding U.S. Appl. No. 16/091,437 dated Nov. 25, 2020.
Office Action issued in corresponding U.S. Appl. No. 16/091,437 dated May 4, 2021.
Yang et al., "High-Performance Aqueous Organic Flow Battery with Quinone-Based Redox Couples at Both Electrodes", Journal of The Electrochemical Society 163(7):A1442-A1449 (2016).
Search Report issued in corresponding EP Appln. No. EP22173705.9 dated Oct. 28, 2022.
Office Action issued in corresponding U.S. Appl. No. 16/967,898 dated Dec. 6, 2022.
Office Action issued in corresponding JP Appln. No. 2021-142062 dated Mar. 16, 2023.
Search Report issued in corresponding EP Appln. No. 22203539.6 dated Mar. 15, 2023.
Search Report issued in corresponding EP Appln. No. 22203648.5 dated Mar. 17, 2023.
Chowdhury Pankaj et al., "Aqueous Photoelectrochemical Reduction of Anthraquinone Disulfonate at Organic Polymer Films", Macromolecular Chemistry and Physics, 217(10):1119-1127 (2016).
Corby B. W. et al., "Clean-chemistry sulfonation of aromatics", J. Chem. Research (S), 26-327 (2002).
Abraham, Ignatious et al. "Recent Advances in 1,4-Benzoquinone Chemistry", Journal of the Brazilian Chemical Society, 22(3):385-421, XP93023984 (2011).
Cheng, Yu-Ting et al. "Production of targeted aromatics by using Diels-Alder classes of reactions with furans and olefins over ZSM-5", Green Chemistry, 14(11):3114-3125, XP055068442 (2012).
Gosselink, Richard et al. "Lignin as a renewable aromatic resource for the chemical industry (Thesis)", 1-196, XP93023331 (2011).
Gosselink, Richard et al. "Lignin as a renewable aromatic resource for the chemical industry (Mini-symposium organized by Wageningen UR Lignin Platform)", Wageningen Contents, 1-26, XP055271803 (2011).
Iskhakova, Gulnara et al. "Diels-Alder reaction between naphthalene and N-phenylmaleimide under ambient and high pressure conditions", 1-10, XP93023886 (2005).
Kamm, Birgit et al. "International biorefinery systems", Pure & Applied Chemistry, 79(11):1983-1997, XP93023254 (2007).
Kim Sungjin et al. "Synthesis of 2,5-Diaminoquinones by One-Pot Copper-Catalyzed Aerobic Oxidation of Hydroquinones and Addition Reaction of Amines", Advanced Synthesis and Catalysis, 351(16):2573-2578, XP93023976 (2009).
Lange, Jean-Paul et al. "Lignocellulose conversion: an introduction to chemistry process and economics", Biofuels, Bioproducts & Biorefining, 1(1):39-48, XP93023325 (2007).
McCarthy, Joseph et al. "Lignin Chemistry, Technology, and Utilization: A Brief History" In: Chemistry, Process Design, and Safety for the Nitration Industry /ACS /Symposium Series, American Chemical Society/Oxford University Press, US, 1-99, XP93023322 (1999).
Ochoa-Gomez, Jose et al. "Industria Quimica Basada en Biomasa implicaciones tecnologicas", 1-106, XP93023315 (2007).
Qi Song et al. "Hydrogenolysis of lignosulfonate into phenols over heterogeneous nickel. catalysts", Chemical Communications, 48(56): 7019-7021, XP055157001 (2012).
Shao, Dan et al. "Electrochemical oxidation of lignin by two typical electrodes: Ti/Sb—SnO2 and Ti/PbO2", Chemical Engeneering Journal, 244:288-295, XP93023751 (2014).
Tarasov, Dmitry et al. "Production of Lignosulfonate in NSSC-Based Biorefinery", Biotechnology Progress, 31(6):1508-1514, XP093023239 (2015).
CAS Registry No. 783281-80-1; 2-Naphthalenesulfonic acid, 1,4-dihydro-3-methoxy-1,4-dioxo-, (2004).
CAS Registry No. 745756-46-1; 2,7-Naphthalenedisulfonic acid, 1,4-dihydro-3-(1-methylethoxy)-1,4-dioxo-, (2004).
Chemical Abstracts Accession No. 2012:1705525 (CAPlus), (2012).
Chemical Abstracts Accession No. 1964:468988 (CAPlus), (1964).
Chemical Abstracts Accession No. 1963:66335 (CAPlus); (1962).
Examination Report from Indian Application No. 202217043089 dated Nov. 13, 2025.
Office Action from JP Application No. 2023-529953 dated Dec. 12, 2025.
International Search Report from corresponding PCT Application No. PCT/EP2020/083958 dated Sep. 7, 2021.
Written Opinion from corresponding PCT Application No. PCT/EP2020/083958 dated Sep. 7, 2021.

(56) References Cited

OTHER PUBLICATIONS

International Search Report from corresponding PCT Application No. PCT/EP2021/085110 dated Jul. 13, 2022.
Written Opinion from corresponding PCT Application No. PCT/EP2021/085110 dated Jul. 13, 2022.
Wang, Y., et al., "One-step electrodeposition of polyaniline/nickel hexacyanoferrate/sulfonated carbon nanotubes interconnected composite films for supercapacitor," J. Solid State Electrochem, 19: 3157-3168 (2015).
Chalamala, B.R., et al., "Redox Flow Batteries: An Engineering Perspective," Proceedings of the IEEE, 102(6): 976-999 (2014).
International Search Report from PCT Application No. PCT/EP2021/062040 dated Feb. 9, 2022.
Written Opinion from PCT Application No. PCT/EP2021/062040 dated Feb. 9, 2022.
Viault, G., et al. (2011). Synthesis of a Focused Chemical Library Based on Derivatives of Embelin, a Natural Product with Proapoptotic and Anticancer Properties. Eur. J. Org. Chem., 2011(7): 1233-1241.
Nagase, Y., et al. (1954). Oxidation of Naphthols with Hydrogen Peroxide in Alkaline Media. Journal of the Pharmaceutical Society of Japan, 74(1): 9-13.
Ettel, V., et al. (1956). Oxidation of pyrocatechol. II. Oxidation in alkaline solution. Chemicke Listy Pro Vedu a Prumysl, Praha, Czechia, 51: 1153-1158.
Xiao, B., et al. (2008). Syntheses and structural characteristics of copper(II)-organic polymers based on N-heterocyclic ligands: A study on the importance of steric factors in the design of potent catalysts. Journal of Molecular Catalysis, 288(1-2): 42-51.
Non-Final Office Action from U.S. Appl. No. 18/036,557 dated Nov. 26, 2025.
Office Action from Japanese Application No. 2023-535447 dated Jan. 9, 2026.
Pillay, Devina et al. (2007). A First Principles Study of the Effects of Sulfur Adsorption on the Activity of Pt, Ni and Pt3Ni. The 2007 Annual Meeting, Salt Lake City.
Zhang et al. (2017). Influence of silica-alumina support ratio on H2 production and catalyst carbon deposition from the Ni-catalytic pyrolysis/ reforming of waste tyres. Waste Management and Research, 35(10): 1-45-1054.
Office Action from U.S. Appl. No. 18/036,558 dated Mar. 17, 2026.
U.S. Appl. No. 18/657,949 dated May 12, 2026.
U.S. Appl. No. 18/038,820 dated May 8, 2026.
Pan, F. et al. (2014). Redox Targeting of Anatase TiO2 for Redox Flow Lithium-Ion Batteries. Adv. Energy Mater., 4: 1400567.
Yan, R. et al. (2018). Redox-Targeting-Based Flow Batteries for Large-Scale Energy Storage. Adv. Mater. 30: 1802406.
Non-Final Office Action from U.S. Appl. No. 18/289,595 dated Apr. 23, 2026.

* cited by examiner

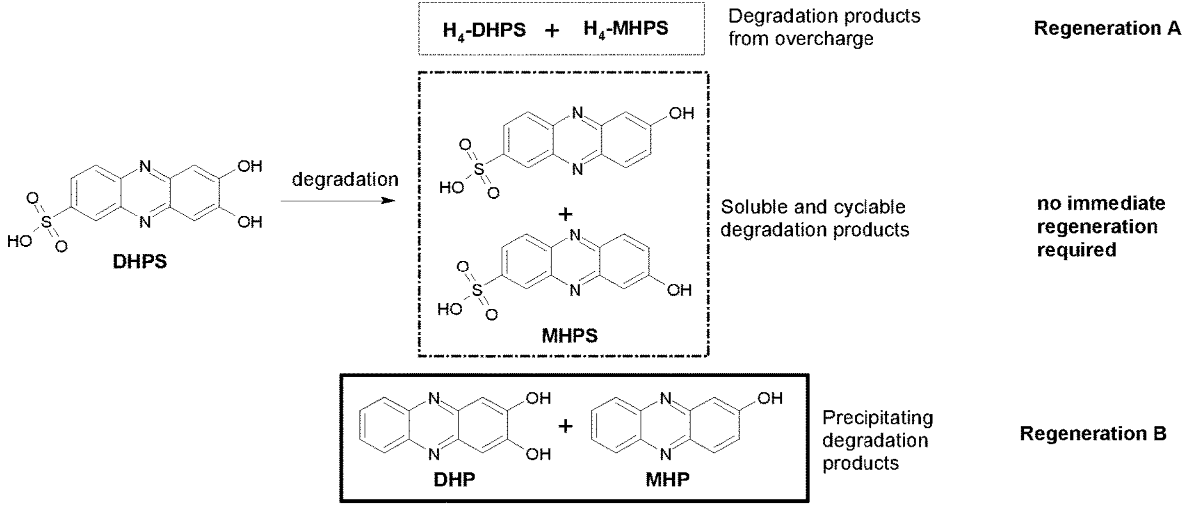
$H_4$-DHPS + $H_4$-MHPS
Degradation products from overcharge
Regeneration A
DHPS
degradation
MHPS
Soluble and cyclable degradation products
no immediate regeneration required
DHP
MHP
Precipitating degradation products
Regeneration B

ELECTROLYTE REGENERATION FOR ORGANIC REDOX FLOW BATTERIES BASED ON WATER-SOLUBLE PHENAZINE-BASED COMPOUNDS

This application is a U.S. National Phase application under 35 U.S.C. § 371 of PCT/EP2020/083927, filed Feb. 30, 2020, the specification of which is hereby incorporated by reference in its entirety into the instant application.

The present invention relates to a process for the regeneration of an electrolyte solution of a redox-flow battery containing at least one (substituted phenazine compound as redox-active material.

Progressive depletion of fossil fuels reserves and concerns resulting from its environmental consequences as the main energy sources have led to an increasing prominence of renewable-energy systems (e.g., solar- and wind-based systems). The intermittent nature of renewable energy sources however makes it difficult to fully integrate these energy sources into electrical grids, resulting in the danger of power outages or negative power prices (B. Dunn, H. Kamath, J.-M. Tarascon, *Science* 2011, 334, 928-935; https://www.cleanenergywire.org/factsheets/why-power-prices-turn-negative, accessed on 9 Aug. 2019). A solution to this problem are large-scale energy storage systems (EES), which are vital for distributed power generation development and grid stabilization. One of the most promising technologies in this field are redox-flow batteries (RFBs), first developed by NASA during the 1970's. RFBs are electrochemical systems that can repeatedly store and convert electrical energy to chemical energy and vice versa when needed. Redox reactions (characterized by individual electrolyte compounds in each half-cell) are employed to store energy in the form of a chemical potential in liquid electrolyte solutions, which are pumped through electrochemical cells.

One of the major challenges of batteries besides the price is the ecological footprint that the battery leaves behind (A. Regett, W. Mauch, U. Wagner, Carbon footprint of electric vehicles—a plea for more objectivity, *FFE* 2018). In the pursuit of a more eco-friendly and sustainable power production leading countries often do not take the ecological consequences into account that are affiliated with the battery production. A rising problem are the ramification of cobalt and lithium mining which are necessary for the growing demand of lithium batteries (https://www.wired.co.uk/article/lithium-batteries-environment-impact). One of the most obvious solutions to reduce the ecological footprint and reduce the price is the recycling of used batteries to reuse the active materials (X. Zhang, L. Li, E. Fan, Q. Xue, Y. Bian, F. Wu, R. Chen, *Chem Soc. Rev.* 2018, 47, 7239-7302). Although this seems to be one of the first options the task is challenging for conventional batteries with solid active material, such as NiCd, NiMH or Li-Ion batteries (A. M. Bernardes, D. C. R. Espinosa, J. A. S. Tenório, *Journal of Power Sources* 2004, 130, 291-298; T. Georgi-Maschler, B. Friedrich, R. Weyhe, H. Heegn, M. Rutz, *Journal of Power Sources* 2012, 207, 173-182; S. Natarajan, V. Aravindan, *ACS Energy Lett.* 2018, 3, 2101-2103). The battery components are hard to separate, volatile and toxic electrolytes evaporate during the process and the active material such as lithium reacts quickly under air and can even combust. The rate of recovery is comparable low, or the material cannot be reused in batteries again. In comparison to conventional batteries, Redox-Flow-Batteries have a major advantage for the recyclability due to their basic setup. For the RFB the posolyte and negolyte are separated from the power unit where the electrochemical reaction takes place and stored in individual tanks. Each electrolyte can be individually accessed directly without disassembly of the battery. The negolyte or posolyte can be exchanged or treated during maintenance or even while the battery is still under operation. However, so far, the only example for the treatment of deactivated organic electrolytes is the oxidation by oxygen of an anthraquinone degradation product outside the system that became inactive upon its dimerization (M.-A. Goulet, L. Tong, D. A. Pollack, D. P. Tabor, S. A. Odom, A. Aspuru-Guzik, E. E. Kwan, R. G. Gordon, M Aziz, *J. Am. Chem. Soc.* 2019, 141, 8014-8019). By oxidation, an intermediate is oxidized yielding the anthraquinone.

Typically, the active material is dissolved in water or an organic solvent. The degradation that occurs over time and leads to capacity fading of the battery is a change of the active material that either leads to a change in solubility, in cell potential and/or to a loss of activity as a redox active substance. The material can either change its electrochemical performance and stay in solution or precipitate and therefore become unavailable for the RFB. Potentially, recycling or treatment of the degraded material could increase the longevity of the battery, decrease the ecological impact and increase the economic benefit of these battery systems.

It is an object of the present invention to provide for a process for recycling redox-active material from an RFB in order to restore the electrochemical performance and or capacity.

Such a recycling process involves at least one of the following partial processes:

i) Chemical or electrochemical treatment of altered or inactive soluble material that stays in solution during the operation of the RFB with the aim to improve the performance and/or to reactivate the material as redox-active compounds for electrical energy storage;

ii) Removal of precipitated altered or inactive material from the battery system and subsequent modification with the aim to improve the solubility and/or to reactivate the material as redox-active compounds for electrical energy storage; and iii) Separation of electrolyte compounds, which have migrated to the electrolyte solution of the other half-cell, e.g. due to operation conditions or loss of function of the semipermeable membrane, within the battery system.

Both organic or inorganic electrolytes for RFBs are subject to structural modification over time and oxidation/reduction battery cycles. The electrolytes' half-life and their degradation pathway depend on the material. In any case, the capacity of the battery decreases as a function of time. The degradation or structural modification can be caused by external factors, such as oxygen or light or, in particular, by internal factors, such as electrochemical reactions during charging and discharging, intramolecular chemical reactions, intramolecular reactions with the solvent or with other molecules or the interaction with the battery components. Essentially, the modified electrolyte compounds may stay in solution and lose their activity or performance, or they may precipitate such that they are excluded from involvement in redox reactions of charging and discharging.

As far as modified soluble compounds are concerned; their recycling may either take place in the battery itself by treatment of the solution within the (operating) battery system or by treatment outside of the (operating) battery system. In case of the treatment within the system, compatibility of the applied recycling process with the battery equipment needs to be ensured. For the external treatment, the modified or inactive compounds may either be isolated from the electrolyte solution or be treated in solution.

Precipitated electrolyte compounds may be isolated in various ways. Filters may be implemented within the battery hydraulic systems to filter off the precipitated material from the battery's electrolyte solutions. Alternatively, an external filter may be foreseen on the tank that is operated continuously or an (mobile) external filter, which is e.g. operated during regular intervals or maintenance. The filtration/separation step may be carried out by a filter press, centrifuge or by membrane filtration. The isolated material may thus be removed from the system and treated in an external vessel.

Another issue having an impact on the battery's capacity is the migration of redox-active electrolyte compounds from their respective half-cell to the other half-cell of the battery, e.g. via the membrane separating the two half-cells. Thereby, the capacity and/or performance in the battery decreases due to loss of difference in potential between the two half-cells. Such migration of redox-active compounds may also result from damaged equipment or an operation failure. Spilled electrolyte can be taken up and mixed electrolyte in the battery needs to be treated in a vessel. The electrolyte compounds of the two half-cells may be physically and/or chemically separated. Upon separation, the restored redox-active electrolyte compounds may be reintroduced into the respective half-cells as posolyte and negolyte in the battery.

The present invention provides a process for the regeneration of an electrolyte solution of a redox-flow battery containing at least one (substituted) phenazine compound, said process comprising at least one of the following steps (a), (b) and (c):

(a) treatment of the electrolyte solution to be regenerated in order to convert organic degradation compounds contained therein to a (substituted) phenazine compound;
(b) removal of precipitated material from the electrolyte solution and subsequent modification of the precipitated organic degradation compounds to obtain a (substituted) phenazine compound; and
(c) separation of redox active compounds other than (substituted) phenazine compounds in particular inorganic electrolytes, from an electrolyte solution containing (substituted) phenazine compounds, and/or separation of (substituted) phenazine compounds from a solution containing redox active compounds other than (substituted) phenazine compounds.

The "phenazine compound" being subject to modification according to the process of the present invention is typically a substituted phenazine, i.e. at least one hydrogen of the basic tricyclic phenazine ring system is substituted by another functional group, e.g. a hydroxy or a sulfonate group. While a "phenazine compound" may in theory occur in both half-cells of a battery, the battery is typically composed of a first half-cell comprising an electrolyte solution containing a "phenazine compound" and a second half-cell comprising an electrolyte solution containing an electrolyte, be it organic or inorganic, other than a "phenazine compound". As far as the following disclosure refers to the regeneration of "phenazine compounds" as electrolytes from an electrolyte solution upon extended operation of a battery, it is understood that it typically is the electrolyte solution of the first half cell, which is regenerated. The other half-cell containing other electrolytes requires other regeneration processes, as e.g. described for metal, e.g. iron, ion complexes further below.

According to a preferred embodiment, the electrolyte solution to be regenerated contains a solvent, which is preferably selected from water, methanol, ethanol, dimethylsulfoxide, acetonitrile, acetone and glycol; or mixtures thereof.

According to a more preferred embodiment, the electrolyte solution to be regenerated is an aqueous solution, which may be exclusively water-based or may contain less than 30% v/v of one or more other water-miscible solvent(s), e.g. ethanol or DMSO.

According to a preferred embodiment, in step (a), the electrolyte solution is treated with an oxidizing agent. Preferably, the oxidizing agent is $O_2$ or $H_2O_2$. Hydrogen peroxide is preferably added to the electrolyte solution as an aqueous solution.

In step (b) the precipitated material is preferably removed from the electrolyte solution by filtration or centrifugation; more preferably by filtration. Filtration may be carried out by suitable filters.

According to a further preferred embodiment, the precipitated material in step (b) is preferably initially hydroxylated, e.g. by treatment with hydrogen peroxide in glacial acetic acid or with 3-chlorobenzoic acid and/or by enzymatic catalysis. The hydroxylated intermediate may, by a next step, be nitrated with e.g. nitric acid, optionally in combination with or without nitrous acid, or it may preferably be sulfonated with e.g. sulfuric acid in combination with or without sulfur trioxide or it may be reacted with an alkylating reagent in the presence of a base. The nitrated intermediate may be converted to the corresponding hydroxylated 5,10-dioxo-5$\lambda^5$,10$\lambda^5$-phenazine compound, e.g. by treatment with a base, and may thereafter e.g. be reduced to the corresponding hydroxylated phenazine compound by treatment with reagents, such as trifluoroacetic anhydride and sodium iodide in acetonitrile. The sulfonated intermediate may be reduced to the corresponding sulfonated phenazine compound, e.g. by treatment with reagents, such as trifluoroacetic anhydride and sodium iodide in acetonitrile. In case the precipitated material comprises polymerized phenazine structures, such a polymerized fraction of the precipitated material may be subject, e.g. upon its separation from other non-polymerized precipitated material, to fragmentation, e.g. by depolymerization under appropriate conditions. The reactions of precipitated material are described in more detail in the following.

For hydroxylation, the phenazine compound may e.g. be converted to the corresponding 5,10-dioxo-5$\lambda^5$,10$\lambda^5$-phenazine compound, e.g. by treatment with hydrogen peroxide in glacial acetic acid or with 3-chlorobenzoic acid at between 20-100° C., preferably between 30-80° C. most preferably between 40-60° C.

The 5,10-dioxo-5$\lambda^5$,10$\lambda^5$-phenazine compound may then e.g. be nitrated with but not limited to nitric acid in combination with or without nitrous acid under cooling to at least at 0° C., at least 10° C., at least 20° C. below room temperature, or under heating to at least at 30° C., at least 40° C., at least 50° C., at least at 60° C., at least 70° C., at least 80° C., at least at 90° C., at least 100° C., at least 110° C., at least at 120° C., at least 130° C., at least 140° C., or at least at 150° C.

The resulting nitrated 5,10-dioxo-5$\lambda^5$,10$\lambda^5$-phenazine compound may then e.g. be converted to the corresponding hydroxylated 5,10-dioxo-5$\lambda^5$,10$\lambda^5$-phenazine compound, e.g. by treatment with a base such as, but not limited to, potassium hydroxide, potassium carbonate, sodium carbonate or sodium hydroxide at temperatures of from 20° C.-150° C., preferably 40° C.-120° C. Finally, the hydroxylated 5,10-dioxo-5$\lambda^5$,10$\lambda^5$-phenazine compound may e.g. be reduced to the corresponding hydroxylated phenazine compound by treatment with reagents such as, but not limited to, trifluoroacetic anhydride and sodium iodide in acetonitrile at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in an aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

In a further embodiment, the phenazine compound may e.g. be converted to the corresponding hydroxylated phenazine compound by treatment with hydrogen peroxide or NAD(P)H/oxygen in presence of an enzyme such as, but not limited to, hydroxylase, or monooxygenase, or PhzA from *Pseudomonas aureofaciens, Pseudomonas aeruginosa* or *Pseudomonas fluorescens*.

According to a another preferred embodiment, the precipitated material in step (b) is sulfonated.

For sulfonation, the phenazine compound may e.g. be converted to the corresponding 5,10-dioxo-5$\lambda^5$,10$\lambda^5$-phenazine compound as described above.

The 5,10-dioxo-5$\lambda^5$,10$\lambda^5$-phenazine compound may then be sulfonated with but not limited to sulfuric acid in combination with or without sulfur trioxide (20-40% $SO_3$) under cooling to at least at 0° C., at least 10° C., at least 20° C. below room temperature, or under heating to at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C.

This sulfonated 5,10-dioxo-5$\lambda^5$,10$\lambda^5$-phenazine compound may then be reduced to the corresponding sulfonated phenazine compound, e.g. by treatment with reagents such as, but not limited to, trifluoroacetic anhydride and sodium iodide in acetonitrile at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

Alternatively, the phenazine compound may e.g. be converted to the corresponding sulfonated phenazine compound by e.g. treatment with, but not limited to, sulfuric acid in combination with or without sulfur trioxide (20-40% $SO_3$) under cooling to at least 0° C., at least 10° C., at least 20° C. below room temperature, or under heating to at least 30° C., at least 40° C., at least 50° C., at least 60° C., at least 70° C., at least 80° C., at least 90° C., at least 100° C., at least 110° C., at least 120° C., at least 130° C., at least 140° C. or at least 150° C.

According to a further preferred embodiment, in step (b) the precipitated material is alkylated.

For alkylation, the phenazine compound may e.g. be reacted with an alkylating reagent in the presence of a base such as, but not limited to, sodium hydroxide, potassium hydroxide, sodium carbonate, potassium carbonate, triethyl amine or sodium methylate at 0-120° C., preferably between 20-80° C. to yield the corresponding alkylated phenazine compound.

According to a further preferred embodiment, in step (b) treatment of the precipitated material comprises fragmentation of polymerized phenazine compounds.

For fragmentation, the polymeric material that precipitates can be fragmented and used as raw material for the electrolyte production. The process may e.g. either be a chemical depolymerization, optionally in the presence of a catalyst, optionally under oxidative or reductive conditions, optionally under pressure and optionally at high temperatures, or a biological depolymerization in the presence of an enzyme or optionally in the presence of an organism.

During cyclisation in redox-flow batteries (RFB) over an extended period of time, electrolytes of each half-cells may cross the semipermeable membrane separating both half-cells such that the initially pure electrolyte solutions of each half-cell are increasingly contaminated by the electrolyte of the respective other half-cell solution, thus decreasing the difference of the redox potential between the half-cells causing a decrease in the capacity of the RFB and eventually loss of functionality. That phenomenon may even be accelerated by whatever damage to the membrane or an accident that destroys part of the system or the tanks or operation failure such that both electrolyte solutions contain both, the positive electrolyte (posolyte) and the negative electrolyte (negolyte). Electrolytes from such mixtures are regenerated by step (c) of the inventive process. i The recovery of the electrolytes from such mixtures and their reuse is desirable for an economic and eco-friendly operation of RFBs, since it avoids the disposal of the electrolyte mixture and the production of new electrolytes.

According to a preferred embodiment, step (c) of the process of the present invention provides a procedure for the separation of phenazine-based electrolytes and inorganic electrolytes, preferably containing transition metal ion complexes (e.g. iron hexacyanide based or halogen ions) from an electrolyte mixture such as an aqueous mixture.

The procedure preferably involves:

(c1) separation of phenazine-based electrolytes from the mixed electrolyte solutions, preferably as a solid, their purification and reuse as electrolytes, and, optionally, (c2) separation of an inorganic electrolyte, preferably transition metal ion complexes (e.g. iron hexacyanides), from the electrolyte solution and their reuse as electrolytes.

Phenazine-based electrolytes may e.g. separated from the solution by means of a decreasing the pH value of the solution and may be purified using acidic wash solutions. The procedure preferably involves a precise adjustment of the pH value, since the purity and yield of the recovered phenazine based electrolyte depends on the adjusted pH value. A second purification step can be applied to further increase the purity of the respective electrolytes.

The pH value is preferably adjusted using inorganic and organic acids (e.g. hydrochloric acid). The highest phenazine recovery yield is achieved from an acidic electrolyte solution with a pH value of 7 and below, preferably pH of 3.5 and lower. The purity is further increased by washing with acidic solution without a decrease of phenazine recovery yield.

A preferably complete removal of the opposite electrolyte from the recovered electrolyte is desirable, since impurities lead to loss in capacity of the RFB.

According to a preferred embodiment, in step (c) the redox active compounds other than phenazine compounds are inorganic redox active compounds including transition metal ions and/or halogen ions, such as $VCl_3/VCl_2$, $Br/ClBr_2$, $Cl_2/Cl^-$, $Fe^{2+}/Fe^{3+}$, $Cr^{3+}/Cr^{2+}$, $Ti^{3+}/Ti^{2+}$, $V^{3+}/V^{2+}$, $Zn/Zn^{2+}$, $Br_2/Br$, $I^{3-}/I^-$, $VBr_3/VBr_2$, $Ce^{3+}/Ce^{4+}$, $Mn^{2+}/Mn^{3+}$, $Ti^{3+}/Ti^{4+}$, $Cu/Cu^+$ and/or $Cu^+/Cu^{2+}$ based compounds.

According to a further preferred embodiment, in step (c) the redox active compounds other than phenazine-based compounds are $M_3[Fe(CN)_6]$ and/or $M_4[Fe(CN)_6]$, wherein M is a cation such as e.g. sodium, potassium or ammonium or mixtures thereof.

According to a preferred embodiment, the process of the present invention comprises at least two of steps (a), (b) and/or (c), in particular (a) and (b). According to a further preferred embodiment, the process of the present invention comprises all three steps (a), (b) and (c).

The present invention further provides a process for the regeneration of an aqueous electrolyte solution of a redox-flow battery containing at least one inorganic redox active compound, said process comprising at least one of the following steps (d), (e) and/or (f):

(d) treatment of the electrolyte solution in order reduce the at least one inorganic redox active compound to the reduced state;

(e) removal of precipitated material from the electrolyte solution and subsequent modification of the precipitated material to obtain at least one water soluble inorganic redox active compound; and/or (f) separation of inorganic redox active compounds from phenazine compounds.

At least one of steps (a), (b) and (c), e.g. steps (a) and (b), may be combined with at least one of steps (c), (d) and (e), e.g. steps (d) and (e).

Preferably, the at least one inorganic redox active compound is selected from those disclosed above, e.g. transition metal ion complexes, such as $M_3[Fe(CN)_6]$ and $M_4[Fe(CN)_6]$, wherein M is a cation such as e.g. sodium, potassium or ammonium or mixtures thereof.

Ferrocyanide may preferably be used as a posolyte for an RFB. In particular, a ferrocyanide salt may exhibit a variety of counterions, such as sodium, potassium or ammonium. For example, potassium/sodium ferrocyanide may be used. The ferrocyanide is the reduced and the ferricyanide the oxidized form representing the discharged and charged state, respectively. Under normal conditions, the posolyte is charged and discharged under releasing or taking up an electron in the same amount as the negolyte. Under certain circumstances this equilibrium is changed, e.g. due to oxidation of the charged negolyte, overreduction of the negolyte during charging or degradation of the posolyte or negolyte. In most cases these factors lead to a higher demand for electrochemical reduction and thus more ferrocyanide is needed. After some time in a symmetric system the posolyte cannot be completely discharged (reduced) and the negolyte cannot be completely charged (reduced) during a battery cycle. The addition of more ferrocyanide or using an excess of ferrocyanide during operation change the electrochemical potential and increases the required volume of the posolyte and therefor is not commercially feasible. A more feasible approach is the addition of a reducing agent, such as sodium sulphite, dithionite, sodium formate or formic acid, directly to the solution that can be metered, does not significantly increase the volume or change the electrochemical potential. The reduction reaction can either be done with a fast reacting reducing agent during a maintenance or a slow reacting reducing agent which is continuously added in small portions to the electrolyte solution.

Further preferably, in step (d) reducing the at least one inorganic redox active compound is carried out using a reducing agent, such as sodium sulfite, potassium sulfite, sodium dithionite, sodium formate and/or ascorbic acid.

More preferably, in step (e) the precipitated material is removed from the electrolyte solution by filtration or centrifugation; especially preferably by filtration.

Further preferably, in step (e) the subsequent modification of the precipitated material involves treatment of the precipitate with a cyanide such as KCN and/or NaCN. The resulting product may then optionally be further treated with a reducing agent, such as but not limited to sodium sulfite, or sodium dithionite, or sodium formate.

More preferably, in step (f) the phenazine compounds are separated from the electrolyte solution by decreasing the pH value of the solution. Further preferably, the pH value is decreased to a pH of 7 or lower; preferably to 3.5 or lower. More preferably, the pH value is decreased using inorganic or organic acids.

Further preferably, the process comprises at least two of steps (d), (e) and/or (f). More preferably, the process comprises all three steps (d), (e) and (f).

Although the present invention is described in detail herein, it is to be understood that this invention is not limited to the particular methodologies, protocols and reagents described herein as these may vary. It is also to be understood that the terminology used herein is not intended to limit the scope of the present invention which will be limited only by the appended claims.

Unless defined otherwise, all technical and scientific terms used herein have the same meanings as commonly understood by one of ordinary skill in the art.

In the following, the features of the present invention will be described. These features are described for specific embodiments. It should, however, be understood that they may be combined in any manner and in any number to generate additional embodiments. The variously described examples and preferred embodiments, should not be construed to limit the present invention to only explicitly described embodiments. This present description should be understood to support and encompass embodiments, which combine the explicitly described embodiments, with any number of the disclosed and/or preferred features. Furthermore, any permutations and combinations of all described features in this application shall be considered supported by the description of the present application, unless it is understood otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

As used herein, the term "negolyte" or "anolyte" refers to the electrolyte, which is in contact with the negative electrode (half-cell A) and the term "posolyte" or "catholyte" refers to the electrolyte, which is in contact with the positive electrode (half-cell B).

Preferably, the term "redox active" refers to the capability of a compound (or a composition comprising the same) to participate in a redox reaction. Such "redox active" compounds typically have energetically accessible levels that allow redox reactions to alter their charge state, whereby electrons are either removed (oxidation-yielding an oxidized form of the compound) from atoms of the compound being oxidized or transferred to the compound being reduced (reduction-yielding a reduced from of the compound). A "redox active" compound may thus be understood as a chemical compound, which may form a pair of an oxidizing and a reducing agent, i.e. a redox pair. Examples for redox active compounds are organic compounds, e.g. (substituted) phenazine compounds or inorganic electrolytes, which include transition metal ions and/or halogen ions, such as $VCl_3/VCl_2$, $Br/ClBr_2$, $Cl_2/Cl^-$, $Fe^{2+}/Fe^{3+}$, $Cr^{3+}/Cr^{2+}$, $Ti^{3+}/Ti^{2+}$, $V^{3+}/V^{2+}$, $Zn/Zn^{2+}$, $Br_2/Br$, $I^{3-}/I^-$, $VBr_3/VBr_2$, $Ce^{3+}/Ce^{4+}$, $Mn^{2+}/Mn^{3+}$, $Ti^{3+}/Ti^{4+}$, $Cu/Cu^+$, $Cu^+/Cu^{2+}$, and others.

For the present invention, at least one of the battery's half-cells employs (substituted) phenazine compounds, typically one of the half-cells.

In general, the term "substituted", e.g. "substituted phenazine", means that at least one hydrogen which is e.g. present on the phenazine ring system is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group, e.g. a "substituted alkyl" has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. Compounds described herein contemplates any and all such combinations in order to arrive at a stable compound. Heteroatoms such as nitrogen may have hydrogen substituents and/or any suitable substituent as described herein which satisfy the valencies of the heteroatoms and results in the formation of a stable moiety. Compounds described herein are not intended to be limited in any manner by the exemplary substituents described herein. "Substituents" are further characterized below, in particular, "substituents" replacing the hydrogen atoms of the phenazine ring system according to General Formulae (1) to (6).

A (preferably substituted) phenazine compound to be employed as an electrolyte by a redox flow battery is preferably selected from compounds that are characterized by any one of General Formulae (1)-(6). They are typically substituted by at least one substituent (other than hydrogen) and include one or more substituents as described herein below. The presence of certain substituents may, e.g., improve the solubility, electrochemical properties and/or stability of the inventive compounds.

General Formula (1)

(a)

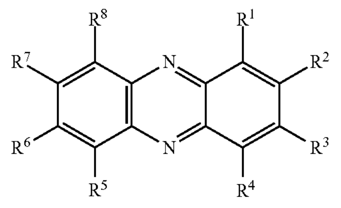

(b)

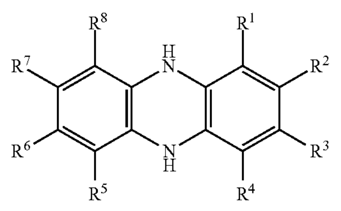

General Formula (2)

(a)

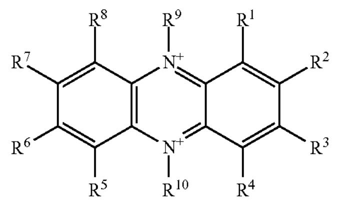

(b)

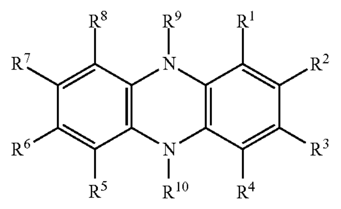

General Formula (3)

(a)

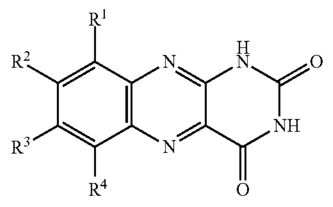

(b)

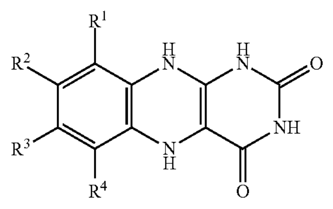

-continued

General Formula (4)

(a)

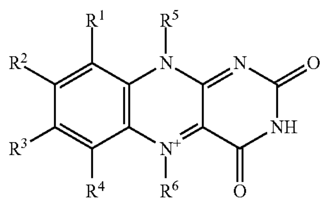

(b)

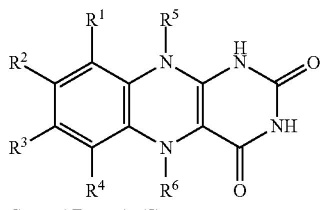

General Formula (5)

(a)

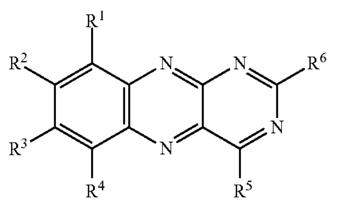

(b)

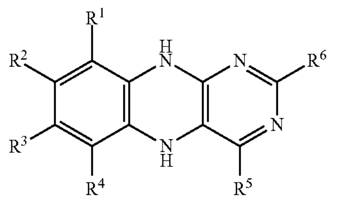

General Formula (6)

(a)

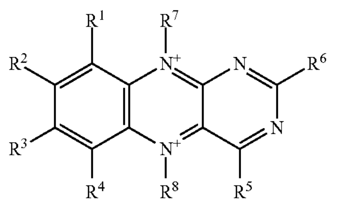

(b)

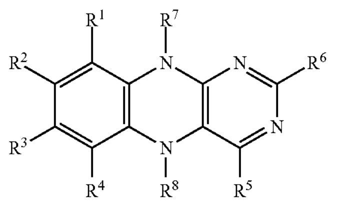

wherein, each $R_1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6)

is independently selected from —H, -Alkyl, -AlkylG$^a$, -Aryl, —$SO_3$H, —$SO_3^-$, —$PO_3H_2$, —OH, —OG$^a$, —SH, -Amine, —$NH_2$, —CHO, —COOH, —COOG$^a$, —CN, —$CONH_2$, —CONHG$^a$, —CONG$^a{}_2$, -Heteroaryl, -Heterocycyl, —NOG$^a$, —N+OG$^a$, —F, —Cl, and —Br, or are joined together to form a saturated or unsaturated carbocycle;

wherein each G$^a$ is independently selected from —H, -Alkyl, -AlkylG$^b$, -Aryl, —$SO_3$H, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_{3+}$, —NHG$^b$, —NG$^b{}_2$, —NG$^b{}_3$+, —CHO, —COOH, —COOAlkyl, —CN, —$CONH_2$, —CONHAlkyl, —$CONAlkyl_2$, -Heteroaryl, -Heterocycyl, —NOG$^b$, —N$^+$OAlkyl, —F, —Cl, and —Br;

wherein each G$^b$ is independently selected from —H, -Alkyl, -Aryl, —$SO_3$H, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —$CONAlkyl_2$, -Heteroaryl, -Heterocycyl, —N$^+$OAlkyl, —F, —Cl, and —Br.

Preferably, each $R^1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6)

may be independently selected from —H, -Alkyl, -AlkylG$^a$, —$SO_3$H, —$SO_3$, —OG$^a$, and —COOH, wherein each G$^a$ is independently selected from —H, -Alkyl, -AlkylG$^b$, -Aryl, —$SO_3$H, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_{3+}$, —NHG$^b$, —NG$^b{}_2$, —NG$^b{}_3$+, —CHO, —COOH, —COOAlkyl, —CN, —$CONH_2$, —CONHAlkyl, —$CONAlkyl_2$, -Heteroaryl, -Heterocycyl, —NOG$^b$, —N$^+$OAlkyl, —F, —Cl, and —Br;

wherein each G$^b$ is independently selected from —H, -Alkyl, -Aryl, —$SO_3$H, —$SO_3^-$, —$PO_3H_2$, —OH, —OAlkyl, —OOH, —OOAlkyl, —SH, —SAlkyl, —$NH_2$, —NHAlkyl, —$NAlkyl_2$, —$NAlkyl_{3+}$, —CHO, —COOH, —COOAlkyl, —CN, —$CONH_2$, —CONHAlkyl, —$CONAlkyl_2$, -Heteroaryl, -Heterocycyl, —N$^+$OAlkyl, —F, —Cl, and —Br.

Typically, "alkyl", "aryl", "heteroaryl", "carbocyclyl", "heterocyclyl", "ether", "thioether" and "amine" or "amino" and other terms are as defined in the following.

The term "alkyl" refers to the radical of saturated hydrocarbon groups, including linear (i.e. straight-chain) alkyl groups, branched-chain alkyl groups, cyclo-alkyl (alicyclic) groups, alkyl-substituted cyclo-alkyl groups, and cyclo-alkyl-substituted alkyl groups.

Preferably, an alkyl group contains less than 30 carbon atoms, more preferably from 1 to 10 carbon atoms ("$C_{1-10}$ alkyl"), from 1 to 9 carbon atoms ("$C_{1-9}$ alkyl"), from 1 to 8 carbon atoms ("$C_{1-8}$ alkyl"), from 1 to 7 carbon atoms ("$C_{1-7}$ alkyl"), or from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group may contain 1 to 4 carbon atoms ("$C_{1-4}$ alkyl"), from 1 to 3 carbon atoms ("$C_{1-3}$ alkyl"), or from 1 to 2 carbon atoms ("$C_{1-2}$ alkyl").

Examples of $C_{1-6}$alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like.

Unless otherwise specified, each instance of an alkyl group is independently unsubstituted (an "unsubstituted alkyl") or substituted (a "substituted alkyl") with one or more substituents (e.g., halogen, such as F).

In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$alkyl, e.g., —$CF_3$, Bn).

Exemplary substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety, or a $G^a$ group as defined herein. Substituents may themselves be substituted. For instance, the substituents of a "substituted alkyl" may include both substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls may be further substituted with alkyls, alkenyls, alkoxys, alkylthios, aminoalkyls, carbonyl-substituted alkyls, —$CF_3$, —CN, and the like.

The term "carbocyclyl" or "carbocyclic" refers to a radical of a non-aromatic cyclic hydrocarbon group having preferably from 3 to 14 ring carbon atoms ("$C_{314}$ carbocyclyl") and zero heteroatoms in the non-aromatic ring system. Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents as defined herein.

The term "heterocyclyl" or "heterocyclic" refers to a radical of a preferably 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment may be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and may be saturated or may contain one or more carbon-carbon double or triple bonds. Heterocyclyl polycyclic ring systems may include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents as defined herein.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) preferably having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as defined herein.

The term "heteroaryl" refers to a radical of a preferably 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment may be a carbon or nitrogen atom, as valency permits. Heteroaryl polycyclic ring systems may include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond. The term "unsaturated" or "partially unsaturated" refers to a moiety that includes at least one double or triple bond.

The term "saturated" refers to a moiety that does not contain a double or triple bond, i.e., the moiety only contains single bonds.

A group is optionally substituted unless expressly provided otherwise. The term "optionally substituted" refers to a group which may be substituted or unsubstituted as defined herein.

The term "aliphatic group" refers to a straight-chain, branched-chain, or cyclic non-aromatic saturated or unsaturated hydrocarbon group and includes as alkyl groups, alkenyl groups, and alkynyl groups.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to group of formula —OR, wherein R is an alkyl group, as defined herein. Exemplary alkoxyl groups include methoxy, ethoxy, propyloxy, tert-butoxy and the like.

The term "aralkyl", as used herein, refers to an alkyl group substituted with an aryl group (e.g., an aromatic or heteroaromatic group).

Alternatively, the term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $—CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" refers to a group which contains a carbon atom connected with a double bond to an oxygen or a sulfur atom. Examples of moieties which contain a carbonyl include aldehydes, ketones, carboxylic acids, amides, esters, anhydrides, etc.

The term "ester" refers to groups or molecules which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "carbonyl" includes groups such as "alkylcarbonyl" groups where an alkyl group is covalently bound to a carbonyl group, "alkenylcarbonyl" groups where an alkenyl group is covalently bound to a carbonyl group, "alkynylcarbonyl" groups where an alkynyl group is covalently bound to a carbonyl group, "arylcarbonyl" groups where an aryl group is covalently attached to the carbonyl group. Furthermore, the term also refers to groups where one or more heteroatoms are covalently bonded to the carbonyl moiety. For example, the term includes moieties such as, for example, aminocarbonyl moieties, (where a nitrogen atom is bound to the carbon of the carbonyl group, e.g., an amide), aminocarbonyloxy moieties, where an oxygen and a nitrogen atom are both bond to the carbon of the carbonyl group (e.g., also referred to as a "carbamate"). Furthermore, aminocarbonylamino groups are also included as well as other combinations of carbonyl groups bound to heteroatoms (e.g., nitrogen, oxygen, sulfur, etc. as well as carbon atoms), such as thiocarbonyl, thiocarboxylic acid and thiolformate. Furthermore, the heteroatom can be further substituted with one or more alkyl, alkenyl, alkynyl, aryl, aralkyl, acyl, etc. moieties.

The term "ether" refers to groups or molecules which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" refers to groups or molecules which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties where an alkyl, alkenyl, or alkynyl group is bonded to a sulfur atom which is covalently bonded to an alkynyl group.

The term "amine" or "amino" includes compounds where a nitrogen atom is covalently bonded to at least one carbon atom or heteroatom. The term "alkyl amino" includes groups and compounds where the nitrogen is bound to at least one additional alkyl group. The term "dialkyl amino" includes groups where the nitrogen atom is bound to at least two additional alkyl groups.

The term "arylamino" and "diarylamino" include groups where the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amine" or "amino" in particular refers to a $—NH_2$ group, preferably including any of its protonation states, such as $—NH_3$.

The term "amide" or "aminocarboxy" includes compounds or moieties which contain a nitrogen atom which is bound to the carbon atom of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties where alkyl, alkenyl, alkynyl and aryl moieties, respectively, are bound to a nitrogen atom which is in turn bound to the carbon of a carbonyl group.

The term "nitro" refers to a $—NO_2$ group.

The term "halo" or "halogen" refers to fluorine (fluoro, —F), chlorine (chloro, —Cl), bromine (bromo, —Br), or iodine (iodo, —I) groups.

The term "thiol" or "sulfhydryl" refers to a —SH group.

The term "hydroxyl" refers to a —OH group, preferably including all of its protonation states, such as $—O^+$.

The term "sulfonyl" refers to a $—SO_3H$ group, preferably including all of its protonation states, such as $—SO_3^-$.

The term "phosphoryl" refers to a $—PO_3H_2$ group, preferably including all of its protonation states, such as $—PO_3H^-$ and $—PO_3^{2-}$.

The term "phosphonyl" refers to a $—PO_3R_2$ group, wherein each R is H or alkyl, provided at least one R is alkyl, as defined herein, preferably including all of its protonation states, such as $—PO_3R$ The term "carboxyl" refers to a —COOH group, preferably including all of its protonation states, such as $—COO^-$.

The term "oxy" refers to a —O group.

Preferably, at least one of the following substituents characterize the substituted phenazine compounds of General Formulae (1) to (6), "alkyl" is selected from linear, branched or cyclic $—C_nH_{2n-o}$ and $—C_nH_{2n-o-m}G^a{}_m$; and/or "aryl" is selected from $—C_6H_5$, $—C_{10}H_7$, $—C_{13}H_8$, $—C_{14}H_9$, $—C_6H_{5-m}G^a{}_m$, $—C_{1-}H_{7-m}G^a{}_m$, $—C_{13}H_{8-m}G^a{}_m$, $—C_{14}H_{9-m}G^a{}_m$; and/or "heteroaryl" is selected from $—C_{5-p}N_pH_{5-p-q}G^a{}_q$, $—C_{6-p}N_pH_{5-p-q}G^a{}_q$, $—C_{7-p}N_pH_{7-p-q}G^a{}_q$, $—C_{8-p}N_pH_{6-p-q}G^a{}_q$, $—C_{9-p}N_pH_{7-p-q}G^a{}_q$, $—C_{10-p}N_pH_{7-p-q}G^a{}_q$, $—C_4OH_{3-q}G^a$q, $—C_6OH_{5-q}G^a{}_q$, $—C_7OH_{4-q}G^a{}_q$, $—C_6O_2H_{3-q}G^a{}_q$, $—C_8OH_{5-g}G^a{}_q$, $—C_4SH_{3-q}G^a{}_q$, $—C_6SH_{5-q}G^a{}_q$, $—C_7SH_{4-q}G^a{}_q$, $—C_6S_2H_{3-q}G^a{}_q$, $—C_8SH_{5-q}G^a{}_q$, $—C_3ON_pH_{3-p-q}G^a{}_q$, $—C_6ON_pH_{5-p-q}G^a{}_q$, $—C_7ON_pH_{4-p-q}G^a{}_q$, $—C_6O_2N_pH_{3-p-q}G^a{}_q$, $—C_8ON_pH_{5-q}G^a{}_q$, $—C_3SN_pH_{3-p-q}G^a{}_q$, $—C_6SN_pH_{5-p-q}G^a{}_q$, $—C_7SN_pH_{4-p-q}G^a{}_q$, $—C_6S_2N_pH_{3-p-q}G^a{}_q$, $—C_6OSN_pH_{3-p-q}G^a{}_q$, $—C_8SN_pH_{5-p-q}G^a{}_q$, $—C_{5-p}N_pH_{6-p-q}G^a{}_q$, $—C_{6-p}N_p+H_{6-p-q}G^a{}_q$, $—C_{7-p}N_p+H_{8-p-q}G^a{}_q$, $—C_{8-p}N_p{}^+H_{7-p-q}G^a{}_q$, $—C_{6-p}N_p{}^+H_{8-p-q}G^a{}_q$, $—C_{10-p}N_p{}^+H_{8-p-q}G^a{}_q$, $—C_3ON_p{}^+H_{4-p-q}G^a{}_q$, $—C_6ON_p{}^+H_{6-p-q}G^a{}_q$, $—C_7ON_p{}^+H_{5-p-q}G^a{}_q$, $—C_6O_2N_p{}^+H_{4-p-q}G^a{}_q$, $—C_8ON_p{}^+H_{6-p-q}G^a{}_q$, $—C_3SN_p{}^+H_{4-p-q}G^a{}_q$, $—C_6SN_p{}^+H_{6-p-q}G^a{}_q$, $—C_7SN_p{}^+H_{5-p-q}G^a{}_q$, $—C_6S_2N_p{}^+H_{4-p-q}G^a{}_q$, $—C_6OSN_p{}^+H_{4-p-q}G^a{}_q$, $—C_8SN_p{}^+H_{6-p-q}G^a{}_q$;

"heterocyclyl" is selected from $—C_{5-p}N_pH_{8-o-pq}G^a{}_q$, $—C_{6-p}N_pH_{10-o-p-q}G^a{}_q$, $—C_{7-p}N_pH_{12-o-p-q}G^a{}_q$, $—C_{8-p}N_pH_{14-o-p-q}G^a{}_q$, $—C_{9-p}N_pH_{16-o-p-q}G^a{}_q$, $—C_{10-p}N_pH_{18-o-p-q}G^a{}_q$, $—C_{5-p}O_pH_{8-o-2p-q}G^a{}_q$, $—C_{6-p}O_pH_{10-o-2p-q}G^a{}_q$, $—C_{7-p}O_pH_{12-o-2p-q}G^a{}_q$, $—C_{8-p}O_pH_{14-o-2p-q}G^a{}_q$, $—C_{9-p}O_pH_{16-o-2p-q}G^a{}_q$, $—C_{10-p}O_pH_{18-o-2p-q}G^a{}_q$, $—C_{5-p}S_pH_{8-o-2p-q}G^a{}_q$, $—C_{6-p}S_pH_{10-o-2p-q}G^a{}_q$, $—C_{7-p}S_pH_{12-o-2p-q}G^a{}_q$, $—C_{8-p}S_pH_{14-o-2p-q}G^a{}_q$, $—C_{9-p}S_pH_{16-o-2p-q}G^a{}_q$, $—C_{10-p}S_pH_{18-o-2p-q}G^a{}_q$, $—C_{5-p}O_lN_pH_{8-o-p-2l-q}G^a{}_q$, $—C_{6-p}O_lN_pH_{10-o-p-2l-q}G^a{}_q$, $—C_{7-p}O_lN_pH_{12-o-p-2l-q}G^a{}_q$, $—C_{8-p}O_lN_pH_{14-o-p-2l-q}G^a{}_q$, $—C_{9-p}O_lN_pH_{16-o-p-2l-q}G^a{}_q$, $—C_{10-p}O_lN_pH_{18-o-p-2l-q}G^a{}_q$, $—C_{5-p}S_lN_pH_{8-o-p-2l-q}G^a{}_q$, $—C_{6-p}S_lN_pH_{10-o-p-2l-q}G^a{}_q$, $—C_{7-p}S_lN_pH_{12-o-p-2l-q}G^a{}_q$, —$C_{8-p}S_lN_pH_{14-o-p-2l-q}G^a_q$, —$C_{9-p}S_lN_pH_{16-o-p-2l-q}G^a_q$, —$C_{10-p}S_lN_pH_{18-o-p-2l-q}G^a_q$; and/or "amine" is selected from —$C_sH_{2s}$—$NH_2$, —$C_sH_{2s}$—$NHG^a$, —$C_nH_{2s}$—$NG^a_2$, —$C_sH_{2s}$—$NG^a_3{}^+$, wherein l=1, 2, 3, 4;

n=1, 2, 3, 4, 5, 6, 7, 8, 9, 10, more preferably n=1, 2, 3, 4, 5, 6, most preferably n=1, 2, 3 or 4;

m=1, 2, 3, 4, 5, 6, 7, 8, 9, 10, more preferably m=1, 2, 3, 4, most preferably m=1 or 2;

o=−1, 2, 3, 5, 7, 9;

p=1, 2, 3, 4, 5, 6, more preferably p=3, 4, 5 or 6;

q=1, 2, 3, 4, 5, more preferably q=1, 2 or 3;

s=1, 2, 3, 4, 5 or 6;

wherein $G^a$ is independently selected from

—H, -Alkyl, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3{}^+$, —$NHG^b$, —$NG^b_2$, —$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+$OAlkyl, —F, —Cl, and —Br;

wherein each $G^b$ is independently selected from

—H, -Alkyl, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_{3+}$, —CHO, —COOH, —COOAlkyl, —CN, —$CONH_2$, —CONHAlkyl, —$CONAlkyl_2$, -Heteroaryl, -Heterocycyl, —$N^+$OAlkyl, —F, —Cl, and —Br.

In some embodiments, each $R^1$-$R^8$ in General Formula (1), each $R^1$-$R^{20}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6) is each independently not selected from —SH, —$NOG^a$ and —N+$OG^a$.

In some embodiments, each $G^a$ in any one of General Formulas (1)-(6) is each independently not selected from —OOH, —OOAlkyl, —SH, —$NOG^b$ and —$N^+$OAlkyl, wherein $G^b$ is as defined above.

In some embodiments, each $G^b$ in any one of General Formulas (1)-(6) is each independently not selected from —OOH, —OOAlkyl, —SH, and —$N^+$OAlkyl.

Particularly preferred compounds may be characterized by General Formula (1), (3) or (4) as defined above.

More preferably, the compounds of any one of General Formulas (1)-(6) may include at least one substituent selected from —H, -Alkyl, -Alkyl$G^a$, —$SO_3H$/—$SO_3{}^-$, —$OG^a$, and —COOH, in particular at least one substituent —$SO_3H$/—$SO_3{}^-$, preferably one or two of —$SO_3H$/—$SO_3{}^-$, wherein each $G^a$ is independently selected from —H, -Alkyl, -Alkyl$G^b$, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3{}^+$, —$NHG^b$, —$NG^b_2$, —$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+$OAlkyl, —F, —Cl, and —Br;

wherein each $G^b$ is independently selected from

—H, -Alkyl, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3{}^-$, —CHO, —COOH, —COOAlkyl, —CN, —$CONH_2$, —CONHAlkyl, —$CONAlkyl_2$, -Heteroaryl, -Heterocycyl, —$N^+$OAlkyl, —F, —Cl, and —Br.

In some embodiments, the substituents may each independently not be —SH, —$NOG^a$ and —N+$OG^a$, wherein $G^a$ is as defined above. In some embodiments, in the above substituent definitions, each $G^a$ is independently not selected from —OOH, —OOAlkyl, —SH, —$NOG^b$ and —$N^+$OAlkyl, wherein $G^b$ is as defined above. In some embodiments, in the above substituent definitions, each $G^b$ is independently not selected from —OOH, —OOAlkyl, —SH, and —$N^+$OAlkyl.

Preferably, "alkyl", "aryl", "heteroaryl", "heterocyclyl" and "amine" are as defined above.

In some embodiments, in the above substituent definitions, each $G^a$ is independently not selected from —OOH, —OOAlkyl, —SH, —$NOG^b$ and —$N^+$OAlkyl, wherein $G^b$ is as defined elsewhere herein.

In some embodiments, in the above substituent definitions, each $G^b$ is independently not selected from —OOH, —OOAlkyl, —SH, and —$N^+$OAlkyl.

Preferably, the compounds of any one of General Formulas (1)-(6) comprise 2-5 substituents as defined above, wherein said 2-5 substituents are preferably not selected from —H. More preferably, the compounds of any one of General Formulas (1)-(6) comprise 3-4 substituents as defined above, wherein said 3-4 substituents are preferably not selected from —H.

Accordingly, in some embodiments, 2-5 or 1-5, more preferably 1, 3 or 4 or 3-4 of $R^1$-$R^8$ in General Formula (1), $R^1$-$R^{10}$ in General Formula (2), $R^1$-$R^4$ in General Formula (3), $R^1$-$R^6$ in General Formula (4), $R^1$-$R^6$ in General Formula (5), and $R^1$-$R^8$ in General Formula (6)

are independently selected from -Alkyl, -Alkyl$G^a$, -Aryl, —$SO_3H$, —$SO_3$, —$PO_3H_2$, —OH, —$OG^a$, —SH, -Amine, —$NH_2$, —CHO, —COOH, —$COOG^a$, —CN, —$CONH_2$, —$CONHG^a$, —$CONG^a_2$, -Heteroaryl, -Heterocycyl, $NOG^a$, —N+$OG^a$, —F, —Cl, and —Br, or are joined together to form a saturated or unsaturated carbocycle, more preferably from —H, -Alkyl, -Alkyl$G^a$, —$SO_3H$/—$SO_3$, —$OG^a$, and —COOH;

wherein each $G^a$ is independently selected from

—H, -Alkyl, -Alkyl$G^b$, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3{}^+$, —$NHG^b$, —$NG^b_2$, —$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+$OAlkyl, —F, —Cl, and Br;

wherein each $G^b$ is independently selected from

—H, -Alkyl, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3{}^+$, —CHO, —COOH, —COOAlkyl, —CN, —$CONH_2$, —CONHAlkyl, —$CONAlkyl_2$, -Heteroaryl, Heterocycyl, —$N^+$OAlkyl, —F, —Cl, and Br.

In some embodiments, each $R^1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6) is independently not selected from —SH, —$NOG^a$ and —N+$OG^a$, wherein $G^a$ is as defined above.

In some embodiments, each $G^a$ in any one of General Formulas (1)-(6) is independently not selected from —OOH, —OOAlkyl, —SH, —$NOG^b$ and —$N^+$OAlkyl, wherein $G^b$ is as defined above.

In some embodiments, each $G^b$ in any one of General Formulas (1)-(6) is independently not selected from —OOH, —OOAlkyl, —SH, and —$N^+$OAlkyl.

In especially preferred embodiments, the compounds of any one of General Formulas (1)-(6) may preferably comprise at least one —$SO_3H$/—$SO_3^-$ group.

In some embodiments, the compounds of any one of General Formulas (1)-(6) may preferably comprise at least one hydroxyl group. If more than one hydroxyl group is represented, they are preferably located at adjacent positions of the ring system.

In some embodiments, the compounds of any one of General Formulas (1)-(6) may preferably comprise at least one alkyl group.

In some embodiments, the compounds of any one of General Formulas (1)-(6) may preferably comprise at least one alkyloxy (alkoxy) group.

In some embodiments, the compounds of any one of General Formulas (1)-(6) may preferably comprise at least one carboxyl group.

In some embodiments, the compounds of any one of General Formulas (1)-(6) may preferably comprise at least one amine group.

Especially preferred are compounds of any one of General Formulas (1)-(6) comprising a —$SO_3H$/—$SO_3^-$ group and at least one other substituent selected from the group consisting of an alkoxy group (e.g. a methoxy group), a hydroxyl group and a carboxyl group. In another preferred embodiment, the compounds comprise by their substitution pattern at least one hydroxyl group, preferably two hydroxyl groups, and at least one other substituent selected from the group consisting of a carboxyl group, a —$SO_3H$/—$SO_3^-$ group, and an alkoxy group. In a further preferred embodiment, the compounds comprise as substituents at least one alkoxy (e.g. a methoxy group), and at least one hydroxyl group. In a further alternative embodiment, the compounds comprise as substituents at least one carboxyl group and at least one —$SO_3H$/—$SO_3^-$ group. In a still further preferred embodiment, the compounds comprise as substituents at least one —$SO_3H$/—$SO_3^-$ group and at least one hydroxyl group. In a still further preferred embodiment, the compounds comprise as substituents at least one —$SO_3H$/—$SO_3^-$ group and at least one alkoxy (e.g. a methoxy group). In a further alternative embodiment, the compounds comprise as substituents at least one carboxyl and at least one hydroxyl group. In a still further preferred embodiment, the compounds comprise as substituents at least one —$SO_3H$/—$SO_3^-$ group, at least one hydroxyl and at least one methoxy group. In another preferred embodiment, the compounds comprise as substituents at least one —$SO_3H$/—$SO_3^-$ group, at least one hydroxyl and at least one carboxyl group. In a still further preferred embodiment, the compounds comprise as substituents at least one alkoxy (e.g. a methoxy group), at least one hydroxyl and at least one carboxyl group. In a preferred embodiment, the inventive compound comprises a methoxy, a hydroxyl and a —$SO_3H$/—$SO_3^-$ group.

In combination with at least one —$SO_3H$/—$SO_3^-$ group, it is also advantageous for the compounds of any one of General Formulas (1)-(6) described above to comprise as substituents at least one alkyl group (e.g. a methyl group), specifically two alkyl groups. Any of the above embodiments comprising an —$SO_3H$/—$SO_3^-$ group (and at least one of a carboxyl group, hydroxyl group and/or alkoxy group) may thus also comprise at least one alkyl group, e.g. one or two alkyl groups, specifically one alkyl group.

The above substitution patterns refers to all of General Formulas (1) to (6), in particular to General Formulas (1) and (2).

Preferred compounds of any one of General Formulas (1)-(6) are e.g. selected from the following compounds (or their reduced counterparts):

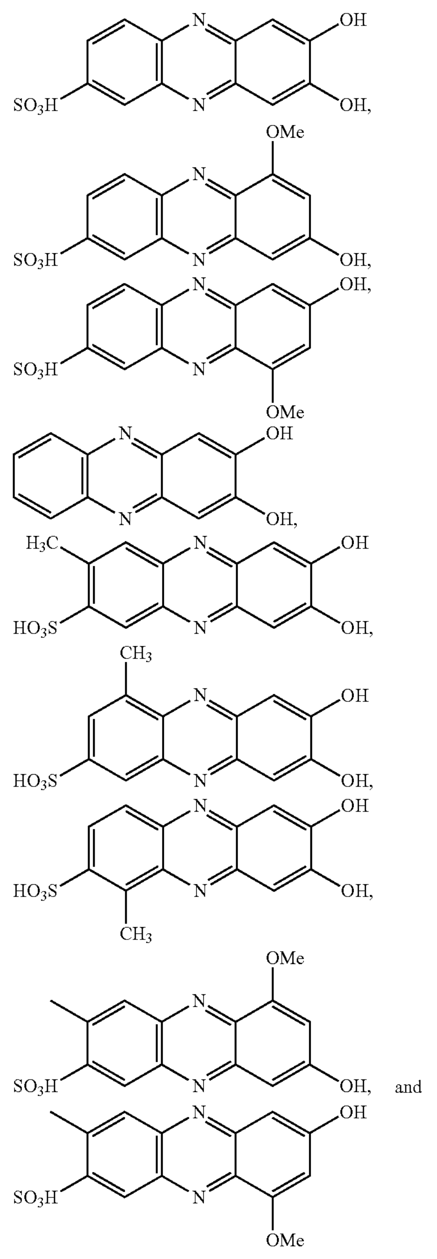

or a combination thereof.

The electrolyte solution of the process of the present invention is a redox flow battery electrolyte. A "(redox flow battery) electrolyte" refers to a substance that is capable of conducting electrical currents via electron transfer in a redox flow battery. Said redox flow battery electrolytes are typically provided as electrolyte solutions. Said "electrolyte solution" comprises at least one (preferably substituted) phenazine-based compound as an electrolyte, and at least one solvent. The at least one phenazine-based compound is dissolved or suspended in a suitable solvent. The solvent may preferably be selected from water, methanol, ethanol, dimethylsulfoxide, acetonitrile, acetone and glycol; or mixtures thereof. The electrolyte solution may comprise further additives, including acids, bases, buffers, ionic liquids, stabilizers, and the like. Such an electrolyte solution containing a (substituted) phenazine as redox-active compound is used e.g. for half-cell A of an RFB, whereas another electrolyte solution, e.g. a solution of an inorganic electrolyte, is used for half-cell B of the RFB.

The at least one (substituted) phenazine-based compound may be used as a posolyte (catholyte) and/or negolyte (anolyte), typically as a negolyte. The term "catholyte" refers to the part or portion of an electrolyte, which is on the cathode side of a redox-flow battery half-cell, whereas the term "anolyte" refers to the part or portion of an electrolyte, which is on the anode side of a redox-flow battery half-cell. In principle, it is conceivable to employ a phenazine-based compound both as catholytes and anolytes in each half-cell (i.e. anode side and cathode side) of the same redox flow battery. However, at least one of the half-cells, e.g. half-cell B, typically represents an electrolyte solution with an electrolyte other than a phenazine-based electrolyte. The electrolyte of half-cell B may be another organic or an inorganic electrolyte. Thereby, an "all-organic" redox flow battery may be provided. Alternatively, the at least one (substituted) phenazine-based compound is utilized either as anolyte (catholyte) in half-cell A, whereas the corresponding catholyte (anolyte) in half-cell B comprises an inorganic redox active species. Examples for such inorganic redox active species include transition metal ions and halogen ions, such as $VCl_3/VCl_2$, $Br^-/ClBr_2$, $Cl_2/Cl^-$, $Fe^{2+}/Fe^{3+}$, $Cr^{3+}/Cr^{2+}$, $Ti^{3+}/Ti^{2+}$, $V^{3+}/V^{2+}$, $Zn/Zn^{2+}$, $Br_2/Br$, $I^{3-}/I^-$, $VBr_3/VBr_2$, $Ce^{3+}/Ce^{4+}$, $Mn^{2+}/Mn^{3+}$, $Ti^{3+}/Ti^{4+}$, $Cu/Cu^+$, $Cu^+/Cu^{2+}$, and others. Metal ions are preferably provided complexed by ligands.

Preferably, the electrolyte solution containing the a phenazine-based compound is used as negolyte (anolyte) in a redox flow battery. In this case, a phenazine-based compound is preferably selected from compounds of general formulas (1 a), (2a), (3a), (4a), (5a) and (6a). In this case, the redox flow battery preferably comprises, as second redox active electrolyte (posolyte (catholyte)), an inorganic material, e.g. a chlorine, bromine, iodine, oxygen, vanadium, chromium, cobalt, iron, manganese, cobalt, nickel, copper, or lead, in particular, bromine or a manganese oxide, a cobalt oxide or a lead oxide, e.g. as ligand complexes, e.g. metal (preferably Fe) complexes, e.g. iron based ligand complexes, such as $X[Fe(CN)_6]$, with X e.g. being an alkali metal ion (e.g. K and/or Na).

The term "aqueous solvent system" or "aqueous solution" refers to a solvent system comprising preferably at least about 20% by weight of water, relative to total weight of the solvent. In some applications, soluble, miscible, or partially miscible (emulsified with surfactants or otherwise) co-solvents may also be usefully present which, for example, extend the range of water's liquidity (e.g., alcohols/glycols). In addition to the redox active electrolytes described herein, the electrolyte solutions may contain additional buffering agents, supporting electrolytes, viscosity modifiers, wetting agents, and the like, which may be part of the solvent system.

Thus, the term "aqueous solvent system" or "aqueous solution" may generally include those comprising at least about 55%, at least about 60 wt %, at least about 70 wt %, at least about 75 wt %, at least about 80%, at least about 85 wt %, at least about 90 wt %, at least about 95 wt %, or at least about 98 wt % water, relative to the total solvent. Sometimes, the aqueous solvent may consist essentially of water, and may be substantially free or entirely free of co-solvents or other (non-target compound) species. The solvent system may be at least about 90 wt %, at least about 95 wt %, or at least about 98 wt % water, or may be free of co-solvents or other (non-target compound) species.

An electrolyte solution may be characterized as having a pH of between about $<0$ and about $>14$. The pH of the electrolyte solution may be maintained by a buffer. Typical buffers include salts of phosphate, borate, carbonate, silicate, trisaminomethane (Tris), 4-(2-hydroxyethyl)-1-piperazineethanesulfonic acid (HEPES), piperazine-N,N'-bis(ethanesulfonic acid) (PIPES), and combinations thereof. A user may add an acid (e.g., HCl, $HNO_3$, $H_2SO_4$ and the like), a base (NaOH, KOH, and the like), or both to adjust the pH of a given electrolyte solution as desired.

Preferably, the electrolyte solution containing the at least one phenazine compound further contains a base such as, e.g., sodium or potassium hydroxide.

EXAMPLES

In the following, the present invention is exemplified for the regeneration of 7,8-Dihydroxyphenazinesulfonic acid (DHPS) as the negolyte and a mixture of sodium and potassium ferrocyanide as the posolyte.

Example 1: Analysis of Degradation Products of DHPS

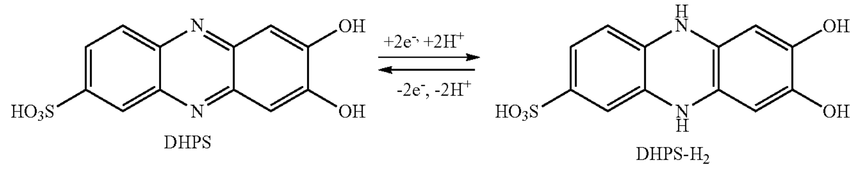

DHPS DHPS-$H_2$

DHPS is soluble in base such as, sodium or potassium hydroxide and can be used as a negolyte in the organic half-cell (e.g. half-cell A) of an RFB. The DHPS is the oxidized and the DHPS-$H_2$ the reduced form representing the discharged and charged state respectively. DHPS can undergo a variety of different chemical and electrochemical degradation reactions which typically occur as a result of extended charging/discharging cycling.

Regeneration of DHPS follows the degradation pathway observed and is characteristic for the DHPS degradation products resulting therefrom. The compounds identified as degradation products are Phenazine-type degradation products and/or over-reduced degradation products. Surprisingly, it has been found by the present inventors that the over-reduced compounds may be regenerated towards the phenazine-type products when applying slightly oxidative conditions.

Identification of Degradation Products:

The following degradation products have been identified via HPLC-MS:

1. Peak at 2.11 min: mass in ESI(−) is 295, in ESI(+) 297. Molar mass of M=296 corresponds to over-reduced DHPS, which is further called $H_4$-DHPS.
2. Peaks at 3.87 and 4.29 min: both peaks have the same pattern in LC-MS: in ESI(−) M−H=279, in ESI(+) M+H=281. Molar mass of M=280 corresponds to over-reduced MHPS (Monohydroxyphenazinesulfonic acid), which is designated as $H_4$-MHPS.
3. Peaks at 5.54 and 6.02 min: both peaks have the same pattern in LC-MS: in ESI(−) M−H=275, in ESI(+) M+H=277. Molar mass of M=276 corresponds to following isomers of MHPS:

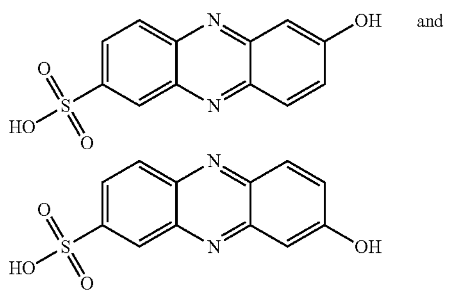

and

4. Peak at 6.97 min: mass in ESI(−) is 211, in ESI(+) 213. Molar mass M=212 corresponds to the following structure (DHP, Dihydroxyphenazine):

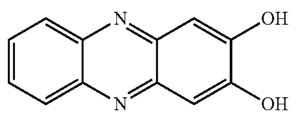 [SMILES: Oc1cc2nc3ccccc3nc2cc1O]

The structure was verified with a standard sample.

5. Peak at 8.04 min: mass in ESI(−) is 195, in ESI(+) 197. Molar mass M=196 corresponds to the following structure (MHP, Monohydroxyphenazine):

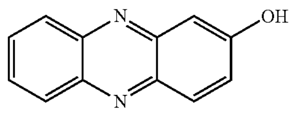 [SMILES: Oc1ccc2nc3ccccc3nc2c1]

The structure of that phenazine degradation product was confirmed by the use of a standard sample as a reference.

During the cycling in the RFB half-cell DHPS is reduced to DHPS-$H_2$. This species may eliminate water to form both isomers of MHPS, depending on which hydroxy group is eliminated. Further, DHPS-$H_2$ may be reduced to $H_4$-DHPS, as detected by HPLC. Finally, overreduction of MHPS leads to two isomers of $H_4$-MHPS. In total, one or more of the above degradation species may be observed as a result of continuous operation of a redox flow battery based on the negolyte DHPS.

In addition, degradation species resulting from the loss of the sulfonic acid group —$SO_3H$ as a substituent of the substituted phenazine compound employed as electrolyte compound were observed: DHP and MHP.

In summary, DHPS loses one or more of its substituents, e.g. one or both sulfonic acid and/or one or more hydroxy group(s) as a result of a larger number of charge/discharge cycles under operation conditions.

The inventors of the present invention observed that the samples of over-reduced species are accessible for oxidation to MHPS and DHPS ($H_4$-MHPS and $H_4$-DHPS) by storing them under air. Also, oxidation was achieved under experimental conditions by chemically reducing DHPS with sodium dithionite to $H_4$-DHPS and $H_4$-MHPS. Such a reference sample, left under air for several hours, allowed for conversion of $H_4$-DHPS and $H_4$-MHPS to DHPS and MHPS. Accordingly, over-reduced phenazine species may be readily regenerated under (e.g. mildly) oxidative conditions.

Solubility and Electrochemical Properties of the Degradation Species.

Various phenazine species (mentioned above and derivable from DHPS) are all electrochemically active, as shown by independent species synthesis. MHP and DHP were synthesized and cyclized in a redox flow cell. Both electrolytes have OCV values of approx. 1,4 V. A solution of DHPS containing approx. 15-20% of MHPS and DHP (as DHPS degraded species) was tested in a RFB cell: The capacity observed during cycling corresponds to the overall concentration of phenazines in solution (DHPS, MHPS and DHP). Thus, MHPS and DHP are also electrochemically active. Their formation (as degradation products of DHPS charge/discharge cycling) was hence found not to decrease the charge capacity in a flow cell.

However, the various degradated species exhibit individual solubilities, depending on the substitution pattern. The solubility of DHPS in a 1:1 mixture of NaOH and KOH with 0.5M free base concentration is about 1.4-1.6M. Loss of a single hydroxy group was found not to significantly decrease DHPS's solubility: both MHPS isomers are well soluble in a 1:1 mixture of NaOH and KOH. In contrast, phenazines without sulfonic acid group were found to be significantly less soluble. For example, solubility of DHP in a 1:1 mixture of NaOH and KOH is reduced to a value of about 0.2-0.4 M, depending on the amount of the free base concentration. Solubility of MHP under such conditions is even lower, i.e. 0.1-0.3M. Surprisingly, the solubility of both DHP and MHP in a DHPS solution up to 0.5 M does not change significantly. Therefore, the phenazine-type degradation species, especially the phenazine-type degradation species DHP and MHP without the sulfonic acid substituent, precipitate without interfering with or impairing the solubility of the solution's DHPS.

In summary, degradation of DHPS after an extended cycling period leads to electrochemically active phenazine degradation species being devoid of one or more substituents and over-reduced species. The inventors determined (i) that over-reduced DHPS species are amenable oxidative to regeneration of reduced phenazine-type compounds even under slightly oxidative conditions. Other phenazine-type degradation species were found to accumulate over time until their solubility limit is reached such that they start to precipitate. MHP and DHP were found to represent degradation species exhibiting the lowest solubility precipitating first.

Based on the data collected by the degradation experiments, three degradation genera were identified as shown in FIG. 1:

1. The over-reduced species $H_4$-MHPS and $H_4$-DHPS, that are e.g. formed under battery overcharging conditions. They may be converted to redox-activity $H_2$-MHPS and $H_2$-DHPS, such that—by straight-forward oxidation—the battery function may be restored, described in more detail as Regeneration A below.

2. MHPS isomers were found to be sufficiently soluble and electrochemically active with their OCV being comparable to DHPS. Thus, such degradation species were found not to require regeneration efforts.
3. Degradation species resulting from an extended cycling period, DHP and MHP. Though they are still electrochemically sufficiently active, they precipitate when reaching their solubility limit upon accumulation in the electrolyte solution. These degradation species have to be separated (e.g. filtered off) and re-converted to more soluble electrolytically active phenazines, described as Regeneration B below.

Example 2: Phenazine Treatment in Solution (Regeneration A)

Example 2.a

Oxygen was bubbled through a solution containing the over-reduced species $H_4$-MHPS and $H_4$-DHPS. Upon oxidation treatment, HPLC analysis confirmed that peaks representing $H_4$-MHPS and $H_4$-DHPS disappeared, whereas peaks of the oxidized species MHPS and MHP increased.

Example 2.b

The solution sample containing over-reduced species $H_4$-MHPS and $H_4$-DHPS was treated by addition of hydrogen peroxide (30 wt % solution in water). HPLC analysis of the reaction mixture proved disappearance of the peaks representing $H_4$-MHPS and $H_4$-DHPS and emergence of an MHPS peak.

In summary, it could be demonstrated that over-reduced phenazine species may be readily regenerated under oxidative conditions.

Example 3: Treatment of Precipitated DHPS Degradation Species (Regeneration B)

The degradation of DHPS was found to generate a variety of degradation species, which precipitate due to their lower solubility. Their solubility decreases as a result of loss of substituents (functional groups other than hydrogen) of DHPS or by polymerization phenomena. Unsubstituted phenazine itself is barely soluble in water. The detected degradation species exhibiting the lowest solubility are DHP and MHP. According to the invention, these species may and are advantageously removed, e.g. be filtered off. They were found to be amenable to chemical regeneration.

Example 3.a Chemical Hydroxylation of MHP to DHP and Trihydroxy Phenazine

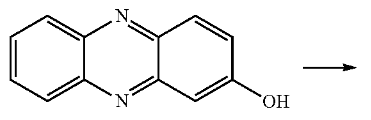

-continued

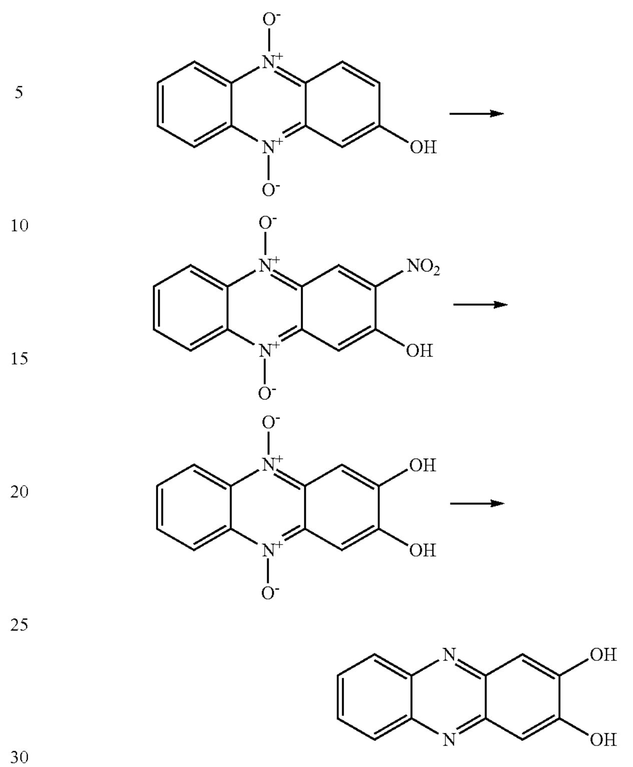

Phenazine-2-ol (an isomer of MHP) was converted to 5,10-dioxo-$5\lambda^5,10\lambda^5$-phenazine-2-ol upon treatment by hydrogen peroxide in glacial acetic acid or with 3-chlorobenzoic acid at between 20-100° C., preferably between 30-80° C. most preferably between 40-60° C. 5,10-dioxo-$5\lambda^5,10\lambda^5$-phenazine-2-ol was then nitrated by nitric acid in combination with or without nitrous acid under cooling to at least 0° C., at least 10° C., at least 20° C. under room temperature, or under heating to at least at 30° C., at least 40° C., at least 50° C. 3-nitro-5,10-dioxo-$5\lambda^5,10^5$-phenazine-2-ol was converted to 5,10-dioxo-$5\lambda^5,10\lambda^5$-phenazine-2,3-diol by treatment with a base such as potassium hydroxide, potassium carbonate, sodium carbonate or sodium hydroxide at temperatures from 20° C.-120° C., preferably 40° C.-100° C. Finally, 5,10-dioxo-$5\lambda^5,10\lambda^5$-phenazine-2,3-diol was reduced to phenazine-2,3-diol by treatment with reagents such as but not limited to trifluoroacetic anhydride and sodium iodide in acetonitrile at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

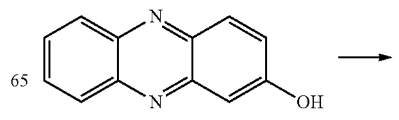

-continued

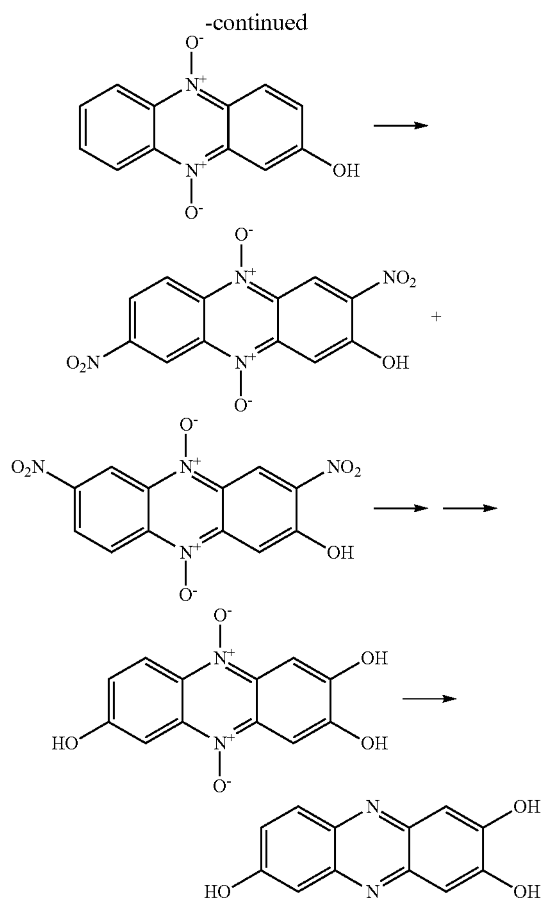

Phenazine-2-ol was converted to 5,10-dioxo-5$\lambda^5$,10$\lambda^5$-phenazine-2-ol by treatment with hydrogen peroxide in glacial acetic acid or with 3-chlorobenzoic acid at between 20-100° C., preferably between 30-80° C. most preferably between 40-60° C. 5,10-dioxo-5$\lambda^5$,10$\lambda^5$-phenazine-2-ol was then nitrated with nitric acid in combination with or without nitrous acid at room temperature, or under heating to at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. The mixture of 3,8-dinitro-5,10-dioxo-5$\lambda^5$,10$\lambda^5$-phenazin-2-ol and 3,7-dinitro-5,10-dioxo-5$\lambda^5$,10$\lambda^5$-phenazine-2-ol was then converted to 5,10-dioxo-5$\lambda^5$,10$\lambda^5$-phenazine-2,3,7-triol by treatment with a base such as potassium hydroxide, potassium carbonate, sodium carbonate or sodium hydroxide at temperatures from 20° C.-150° C., preferably 40° C.-120° C. Finally, 5,10-dioxo-5$\lambda^5$,10$\lambda^5$-phenazine-2,3,7-triol was reduced to phenazine-2,3,7-triol by treatment with reagents such as trifluoroacetic anhydride and sodium iodide in acetonitrile at rt, or titanium (IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

Example 3.b Enzymatic Hydroxylation of MHP to DHP

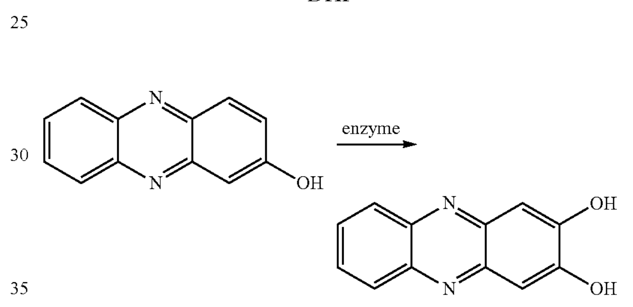

Phenazine-2-ol was converted to phenazine-2,3-diol by treatment with hydrogen peroxide or NAD(P)H/oxygen in the presence of a enzyme, such as hydroxylase, or monooxygenase, or PhzA from *Pseudomonas aureofaciens, Pseudomonas aeruginosa* or *Pseudomonas fluorescens.*

Example 3.c Sulfonation of MHP

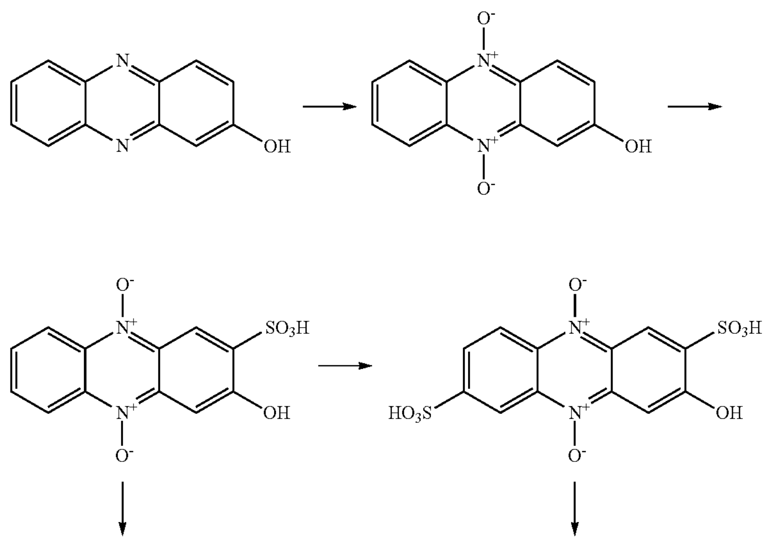

-continued

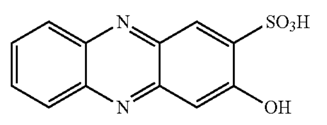

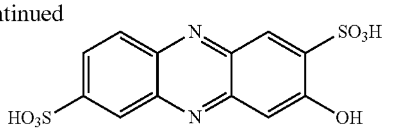

Phenazine-2-ol was converted to 5,10-dioxo-5λ$^5$,10λ$^5$-phenazine-2-ol by treatment with hydrogen peroxide in glacial acetic acid or with 3-chlorobenzoic acid at between 20-100° C., preferably between 30-80° C. most preferably between 40-60° C. 5,10-dioxo-5λ$^5$,10λ$^5$-phenazine-2-ol was then sulfonated with sulfuric acid in combination with or without sulfur trioxide (20-40% $SO_3$) under cooling to at least at 0° C., at least 10° C., at least 20° C. under room temperature, or under heating to at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. 3-hydroxy-5,10-dioxo-5λ$^5$,10λ$^5$-phenazine-2-sulfonic acid and 3-hydroxy-5,10-dioxo-5λ$^5$,10λ$^5$-phenazine-2,7-disulfonic acid were then reduced to 3-hydroxyphenazine-2-sulfonic acid and 3-hydroxyphenazine-2,7-disulfonic acid, correspondingly, by treatment with reagents such as trifluoroacetic anhydride and sodium iodide in acetonitrile at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

Example 3.d Alkylation of DHP

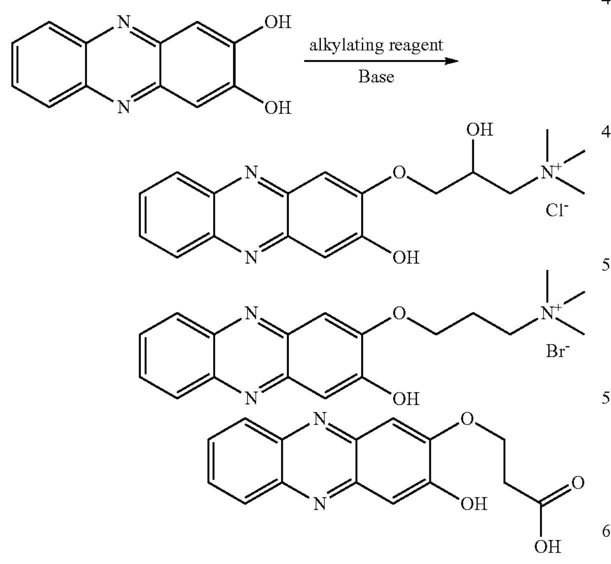

Phenazine-2,3-diol was reacted with different alkylating reagents (Bitte die verwendeten Alkylierungsmittel angeben) in the presence of a base such as sodium hydroxide, potassium hydroxide, sodium carbonate, potassium carbonate, triethyl amine or sodium methylate at 0-120° C., preferably between 20-80° C. to yield 2-hydroxy-3-[(3-hydroxyphenazine-2-yl)oxy]-N,N,N-trimethylpropan-1-aminium chloride, or 3-[(3-hydroxyphenazine-2-yl)oxy]-N,N,N-trimethylpropan-1-aminium bromide, or 3-[(3-hydroxyphenazine-2-yl)oxy]propanoic acid.

Example 3.e Sulfonation of DHP to DHPS

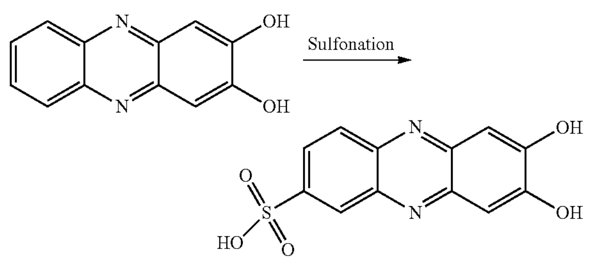

Phenazine-2,3-diol was converted to 7,8-dihydroxyphenazine-2-sulfonic acid by treatment with sulfuric acid in combination with or without sulfur trioxide (20-40% $SO_3$) under cooling to at least at 0° C., at least 10° C., at least 20° C. under room temperature, or under heating to at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C.

Example 3.f Fragmentation of Polymerized Phenazine

Polymeric active material that precipitates could be fragmented and used as raw material for the electrolyte production. The process was either a chemical depolymerization, optionally in the presence of a catalyst, optionally under oxidative or reductive conditions, optionally under pressure and optionally at high temperatures, or a biological depolymerization in the presence of an enzyme or, optionally, in the presence of an organism.

In summary it has been shown that phenazine compounds may be converted to a variety of soluble species by various measures.

Example 4: Regeneration of Ferrocyanide in Solution

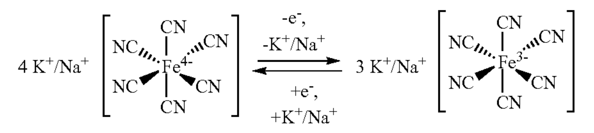

In the present example, a mixture of potassium and sodium ferrocyanide is used as a posolyte for an RFB. The ferrocyanide is the reduced and the ferricyanide the oxidized form representing the discharged and charged state, respectively.

Example 4.a Ferrocyanide Treatment in Solution

The required amount of regeneration reagent (reducing agent) was added to a solution containing 347 mM of sodium/potassium hexacyanoferrate (II) and 257 mM sodium/potassium hexacyanoferrate (III) (SOC 43%) and 0.49 mM base (1:1 mixture of KOH and NaOH). The mixture was stirred for a given time at a given temperature (see Table below). The solution was analyzed by UV-Vis, and the base concentration was determined by titration.

Reaction Equations with Different Regeneration Reagents:

Sodium sulfite: 0.5 eq $Na_2SO_3$ is required for the reduction of 1 eq $Na_3[Fe(CN)_6]$

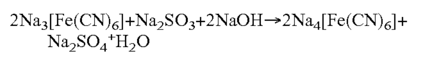

$$2Na_3[Fe(CN)_6]+Na_2SO_3+2NaOH \rightarrow 2Na_4[Fe(CN)_6]+Na_2SO_4{}^{+}H_2O$$

Sodium dithionite: 0.16 eq $Na_2S_2O_4$ is required for the reduction of 1 eq $Na_3[Fe(CN)_6]$

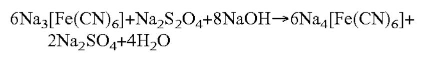

$$6Na_3[Fe(CN)_6]+Na_2S_2O_4+8NaOH \rightarrow 6Na_4[Fe(CN)_6]+2Na_2SO_4+4H_2O$$

Sodium formate: 0.5 eq HCOONa is required for the reduction of 1 eq $Na_3[Fe(CN)_6]$

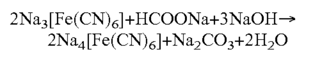

$$2Na_3[Fe(CN)_6]+HCOONa+3NaOH \rightarrow 2Na_4[Fe(CN)_6]+Na_2CO_3+2H_2O$$

Results:

| Regeneration reagent | Amount | Reaction conditions | SOC and hexacyanoferrate concentration |
|---|---|---|---|
| Sodium sulfite $Na_2SO_3$ | 125 mM | Room temperature, 2 h | SOC 2%, $c(Fe(CN)_6{}^{2})$ = 591 mM |
| Potassium sulfite $K_2SO_3$ | 125 mM | Room temperature, 2 h | SOC 0%, $c(Fe(CN)_6{}^{2})$ = 587 mM |
| Sodium dithionite $Na_2S_2O_4$ | 50 mM | Room temperature, 2 h | SOC 1%, $c(Fe(CN)_6{}^{2})$ = 594 mM |
| Sodium formate HCOONa | 125 mM | 40° C., 43 h | SOC 8%, $c(Fe(CN)_6{}^{2})$ = 538 mM |
| Ascorbic acid (as 0.5M solution in 1M KOH/NaOH) | 300 mM | Room temperature, 3 h | SOC 0%, $c(Fe(CN)_6{}^{2})$ = 415 mM |

In summary it was shown that the concentration of sodium/potassium hexacyanoferrate (II) in the solution treated was dramatically increased.

Example 5: Treatment of an Iron Complex Precipitate Resulting from an Iron Complex Electrolyte Ferrocyanide is prone to degradation due to external factors such as light, pH, electrochemical reactions, chemical reactions or physical reactions over time. As a result of exposure to such conditions, ferrocyanide changes its chemical or physical properties, such as solubility, electrochemical potential or activity. Reduction of solubility may also be involved such that degradation species may precipitate. Precipitated material may be filtered off and used as an iron source for the production or regeneration of ferrocyanide.

Example 5.a

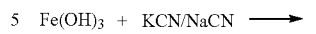

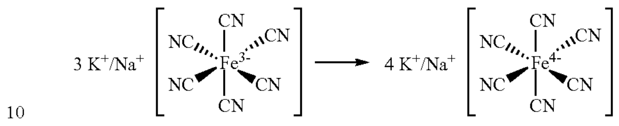

The precipitate of iron (III) hydroxide was treated with a mixture of sodium cyanide (3 eq) and potassium cyanide (3 eq) at 0-120° C., preferably between 20-80° C. to yield sodium/potassium hexacyanoferrate (III). Sodium/potassium hexacyanoferrate (III) was then reduced to sodium/potassium hexacyanoferrate (II) by treatment with a reducing reagent such as sodium sulfite, or sodium dithionite, or sodium formate.

Example 6: Recovery of Negolytes and Posolytes from their Respective Solutions

In the following example the separation of negolytes from a posolyte solution or, vice versa, the separation of posolytes from a negolyte solution is shown:

In the following example, the procedure is described for the recovery of (i) DHPS and (ii) potassium/sodium ferrocyanide by treating solutions (as they may occur upon an extended period of cycling in either solution of half-cell A or half-cell B) containing both of (i) and (ii), respectively.

This procedure involves the following steps:

a) DHPS was precipitated as acid or as salt from a 1:1 (v/v) mixture of DHPS (0.5 M DHPS in 0.5 M base (NaOH/KOH n/n=1/1)). Potassium/sodium ferrocyanide (0.65 M iron(II) hexacyanide in 0.23 M base (NaOH/KOH n/n=1/1)) by addition of an acid to the electrolyte solution. The precipitated phenazine was separated and further purified. The purified DHPS could be used for preparing an electrolyte solution.

b) The remaining acidic solution contained the iron hexacyanide. Simple addition of base converted the acidic solution to the basic electrolyte. Further separation and purification of the iron hexacyanide was achieved by crystallization from the solution at lower temperatures, preferably below 20° C., or precipitation by addition of inorganic or organic salts that lower the solubility of the hexacyanide. The purified iron hexacyanide can be re-used for preparing an electrolyte solution.

Example 6a: Impact of the pH Value on the Phenazine Purity and Recovery Yield

Hydrochloric acid (37%) was added at room temperature to a mixture of 5 mL DHPS (0.5 M DHPS in 0.5 M base (NaOH/KOH n/n=1/1)) and 5 mL potassium/sodium ferrocyanide (0.65 M iron(II) hexacyanide in 0.23 M base (NaOH/KOH n/n=1/1)) to adjust the solution to different pH values. The precipitated electrolyte mixture was dissolved in 2 M potassium hydroxide to a volume on 10 mL. The electrolyte concentrations were determined by HPLC and are summarized in Table 1.

TABLE 1

Recovery of phenazine (sulfonic acid and sulfonate) from a ferrocyanide/DHPS mixture by addition of hydrochloric acid.

| pH value | Iron hexacyanide concentration of the precipitate [mM] | Phenazine concentration of the precipitate [mM] | Phenazine recovery [%] | Phenazine purity [%] |
|---|---|---|---|---|
| 7.3 | 44.4 | 68.2 | 27 | 61 |
| 5.9 | 85.3 | 185.6 | 74 | 69 |
| 3.2 | 138.2 | 243.6 | 97 | 64 |
| 2.2 | 127.7 | 251.7 | 100 | 66 |
| 1.5 | 97.2 | 244.3 | 98 | 72 |

As can be taken from this table, by lowering the pH to less than 6, the recovery yield was significantly improved.

Example 6b: Influence of the pH Value and an Additional Washing of the Precipitate with Diluted Hydrochloric Acid on the Phenazine Purity and Recovery Yield Hydrochloric acid (37%) was added at room temperature to a mixture of 5 mL DHPS (0.5 M DHPS in 0.5 M base (NaOH/KOH n/n=1/1)) and 5 mL potassium/sodium ferrocyanide (0.65 M iron(II) hexacyanide in 0.23 M base (NaOH/KOH n/n=1/1)) to adjust the solution to different pH values. The precipitated electrolyte mixture was washed with 1.2 M hydrochloric acid and dissolved in 2 M potassium hydroxide to a volume on 10 mL. The electrolyte concentrations were determined by HPLC and are summarized in Table 2.

TABLE 2

Recovery of phenazine (sulfonic acid and sulfonate) from a ferrocyanide/DHPS mixture by addition of hydrochloric acid and an additional washing of the precipitate with diluted hydrochloric acid.

| pH value | ferrocyanide concentration of the precipitate [mM] | Phenazine concentration of the precipitate [mM] | Phenazine recovery [%] | Phenazine purity [%] |
|---|---|---|---|---|
| 2.2 | 21 | 250 | 100 | 92 |
| 0.5 | 22 | 226 | 90 | 91 |

In summary, it was that it is possible to separate mixed electrolytes by varying the pH value.

Technical Supportings:

All chemicals and solvents were used as bought.

Electrochemical Tests:

For electrochemical characterization, a small laboratory cell was used. A graphite felt (with an area of 6 $cm^2$, 6 mm in thickness, supplier: SGL GFA 6EA) was employed as both the positive and negative electrode, and a cation exchange membrane (630K or 620PE, supplier: fumatech) was used to separate the positive and negative electrolytes. The membrane was conditioned in 0.5 M KOH/NaOH (50/50) for at least 150 h prior to each test. Electrolyte volumes range from 12 to 50 mL. The electrolytes were pumped by peristaltic pumps (Drifton BT100-1 L, Cole Parmer Ismatec MCP and BVP Process IP 65) at a rate of 24 mL/min to the corresponding electrodes, respectively. Electrochemical testing was performed on a BaSyTec (BaSyTec GmbH, 89176 Asselfingen, Germany) or a Bio-Logic (Bio-Logic Science Instruments, Seyssinet-Pariset 38170, France) battery test system by polarization curves, which were recorded in the charged state by galvanostatic holds and constant-current charge-discharge cycles. For cycling, the cell was charged at a current density of 25 mA/$cm^2$ up to 1.7 V and discharged at the same current density down to 0.8 V cut-off.

Analytical Methods:

UV-VIS Spectroscopy

Parameter for UV-Vis measurement:

Device: PerkinElmer Lambda25

Layer thickness cuvette: 10 mm

Temperature: 22.5° C.±2.5° C.

Detection: 200-700 nm

Scan speed: 480 nm/min

Slit: 1 nm

Solvent for measurement: $H_3PO_4$ (25 mM)

An aqueous solution of the substance (0.1 M) was diluted with phosphorus acid (25 mM) to a final substance concentration of 2 μM. A "Hellma Makro UV-6030" cuvette was used for the measurement.

Infrared Spectroscopy

Parameter for IR measurement:

Device: Bruker Vector 22

Temperature: 22.5° C.±2.5° C.

Range: 550-4000 $cm^{-1}$

A small amount of the substance was applied to the crystal of the ATR unit.

High-Performance Liquid Chromatography (HPLC)

Device: Hitachi Chromaster

Column: Merck Chromolith® HighResolution RP-18e 4.6×100 mm

Temperature: 40° C.

Detection: 250/280 nm

Solvent sample: Ammonium acetate 0.2 M

Concentration sample: <0.5 mg/ml

Inj. Volume: 2 μl

| | Time [min] | $H_2O$ % | $H_3PO_4$ (0.5M) % | Acetonitrile % | Flow [ml/min] |
|---|---|---|---|---|---|
| Gradient: | 0.00 | 95.0 | 5.0 | 0.0 | 2,000 |
| | 0.50 | 95.0 | 5.0 | 0.0 | 2,000 |
| | 6.50 | 75.0 | 5.0 | 25.0 | 2,000 |
| | 7.00 | 5.0 | 5.0 | 90.0 | 2,000 |
| | 7.50 | 5.0 | 5.0 | 90.0 | 2,000 |
| | 8.00 | 95.0 | 5.0 | 0.0 | 2,500 |
| | 10.00 | 95.0 | 5.0 | 0.0 | 2,500 |

Mass Spectrometry

Parameter for MS measurement:

Device: Waters micromass triple quad

Detection: 50-1000 m/z

Ionization mode: ESI−

The invention claimed is:

1. A process for the regeneration of an electrolyte solution of a redox-flow battery containing at least one phenazine compound, the process comprising:

treating the electrolyte solution to be regenerated to convert organic degradation compounds contained therein to a phenazine compound;

wherein the phenazine compound is selected from the group consisting of:

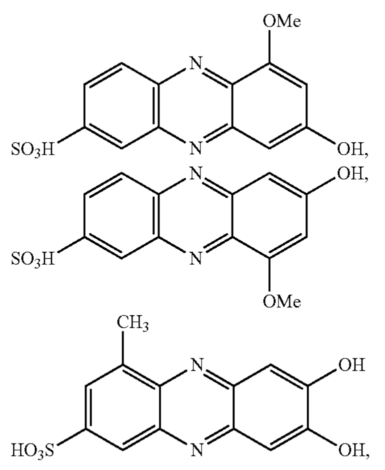

-continued

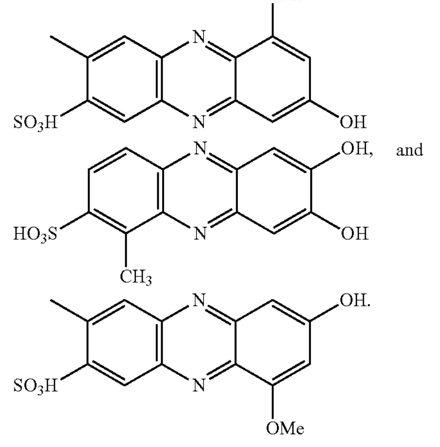

and

2. The process of claim 1, wherein the electrolyte solution is an aqueous solution.

3. The process of claim 1, wherein the electrolyte solution further contains a base, wherein the base is sodium or potassium hydroxide.

4. The process of claim 1, wherein the electrolyte solution is treated with an oxidizing agent.

5. The process of claim 4, wherein the oxidizing agent is $O_2$ or $H_2O_2$.

* * * * *